(12) United States Patent
Hansen

(10) Patent No.: US 9,010,329 B2
(45) Date of Patent: Apr. 21, 2015

(54) ELECTRONICALLY-CONTROLLED, HIGH PRESSURE FLOW CONTROL VALVE AND METHOD OF USE

(75) Inventor: Brian N. Hansen, Longmont, CO (US)

(73) Assignee: Aerophase, Longmont, CO (US)

(*) Notice: Subject to any disclaimer, the term of this patent is extended or adjusted under 35 U.S.C. 154(b) by 1202 days.

(21) Appl. No.: 12/703,351

(22) Filed: Feb. 10, 2010

(65) Prior Publication Data

US 2010/0199982 A1 Aug. 12, 2010

Related U.S. Application Data

(60) Provisional application No. 61/151,393, filed on Feb. 10, 2009.

(51) Int. Cl.
| | |
|---|---|
| A62B 9/02 | (2006.01) |
| A61M 11/00 | (2006.01) |
| F16K 31/02 | (2006.01) |
| A61M 15/00 | (2006.01) |
| F16K 1/14 | (2006.01) |
| A61M 16/00 | (2006.01) |
| B65D 83/54 | (2006.01) |

(52) U.S. Cl.
CPC ............. *F16K 31/02* (2013.01); *A61M 15/009* (2013.01); *A61M 2016/0021* (2013.01); *A61M 2202/0225* (2013.01); *A61M 2205/0266* (2013.01); *A61M 2205/8225* (2013.01); *B65D 83/54* (2013.01); *F16K 1/14* (2013.01); *A61M 15/008* (2013.01)

(58) Field of Classification Search
USPC ..................... 236/12.11; 600/399; 604/891.1; 606/181; 128/205.24
See application file for complete search history.

(56) References Cited

U.S. PATENT DOCUMENTS

| | | | | |
|---|---|---|---|---|
| 2,930,578 | A | * | 3/1960 | Piros .............................. 251/332 |
| 3,624,821 | A | * | 11/1971 | Henderson .................... 417/137 |
| 4,970,093 | A | | 11/1990 | Sievers et al. |
| 4,973,024 | A | * | 11/1990 | Homma ......................... 251/11 |
| 5,301,664 | A | * | 4/1994 | Sievers et al. ............ 128/200.23 |
| 5,639,441 | A | | 6/1997 | Sievers et al. |
| 6,024,340 | A | * | 2/2000 | Lazarus et al. ........... 251/129.06 |
| 6,032,836 | A | | 3/2000 | Hiscocks et al. |
| 6,470,872 | B1 | | 10/2002 | Tiberius et al. |
| 6,701,909 | B2 | | 3/2004 | Tiberius et al. |
| 6,892,718 | B2 | | 5/2005 | Tiberius et al. |
| 7,028,698 | B2 | | 4/2006 | Hansen et al. |

(Continued)

*Primary Examiner* — Jason Flick
(74) *Attorney, Agent, or Firm* — Porter Wright Morris & Arthur LLP

(57) ABSTRACT

A fluid flow control valve comprises (a) a high pressure region adapted to contain a fluid at its supercritical or near-critical temperature and pressure conditions and connected via an orifice to a low pressure region, (b) a seat adjacent the orifice, (c) a sealing element positionable against the seat to form a seal between the high pressure region and the low pressure region, and (d) an electrically and/or electronically controlled actuator operable to move the sealing element against and/or away from the seat to allow control of fluid flow from the high pressure region to the low pressure region. In a specific embodiment, the high pressure region contains a fluid at its supercritical or nearcritical temperature and pressure conditions. The valve may be used, for example, to provide very low flow rates, for example, for supercritical fluid chromatography, supercritical fluid extraction, critical point drying, supercritical fluid cleaning, and supercritical fluid separation methods. In another embodiment, the valve is suitable for use in methods of delivering a biologically active substance to a patient in need thereof.

22 Claims, 22 Drawing Sheets

(56) References Cited

U.S. PATENT DOCUMENTS

| | | |
|---|---|---|
| 7,055,793 B2 * | 6/2006 | Biehl et al. ............. 251/11 |
| 7,168,597 B1 * | 1/2007 | Jones et al. ............. 222/402.2 |
| 7,299,801 B2 | 11/2007 | Hodson |
| 7,478,632 B2 | 1/2009 | Halmone |
| 7,748,378 B2 | 7/2010 | Hodson |
| 8,104,497 B2 * | 1/2012 | Unger et al. ............. 137/15.05 |
| 8,167,172 B2 | 5/2012 | Yeames |
| 2004/0257403 A1 * | 12/2004 | Silverbrook ............. 347/54 |
| 2008/0027478 A1 * | 1/2008 | Connors et al. ............. 606/192 |
| 2009/0007972 A1 * | 1/2009 | Lum et al. ............. 137/468 |
| 2009/0138032 A1 * | 5/2009 | Freeman et al. ............. 606/181 |
| 2012/0045976 A1 * | 2/2012 | Roser et al. ............. 451/358 |

\* cited by examiner

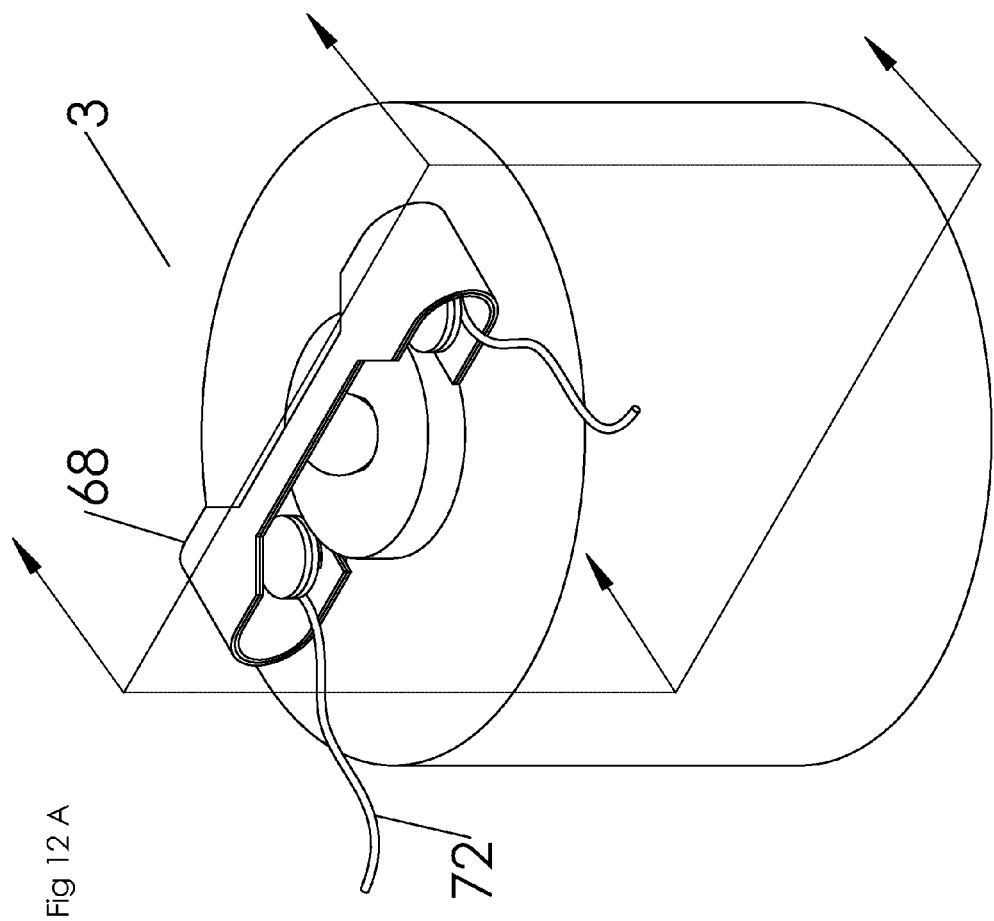

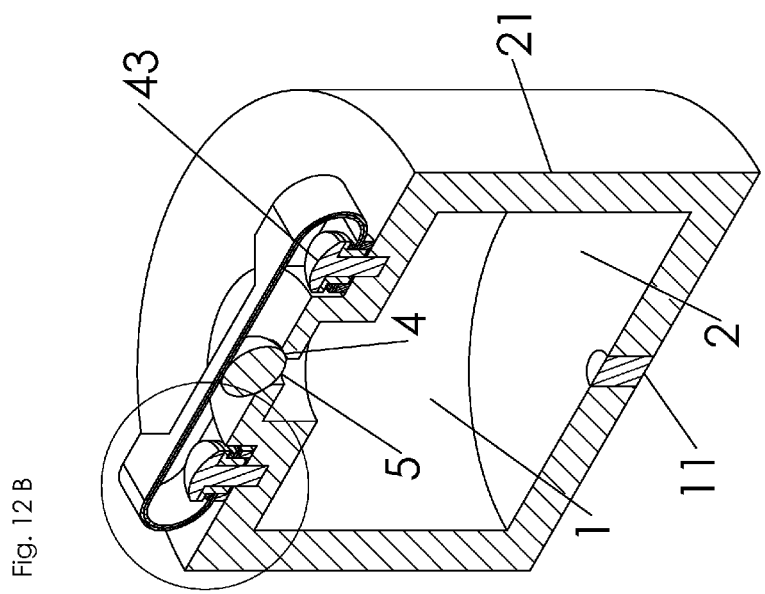

55

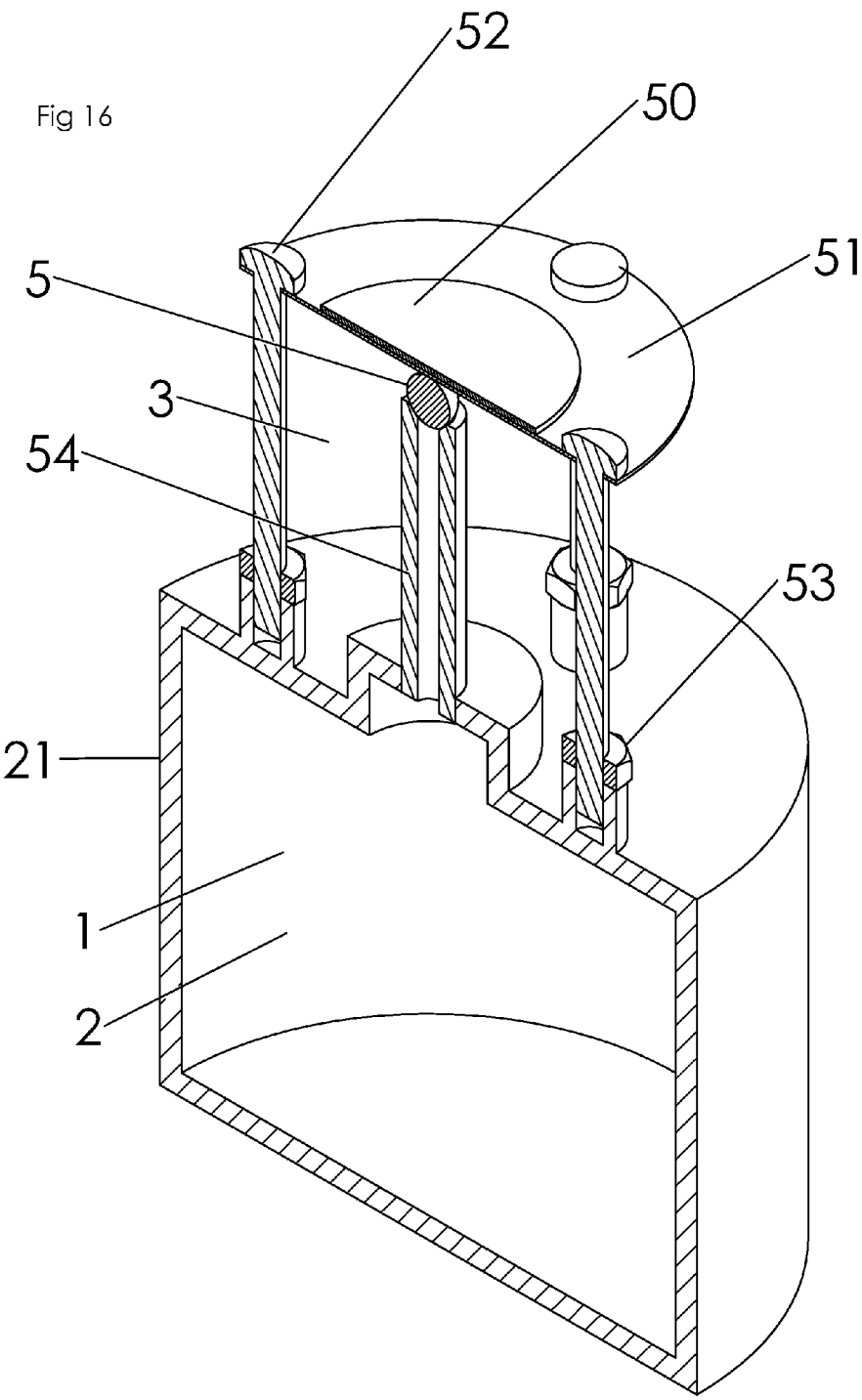

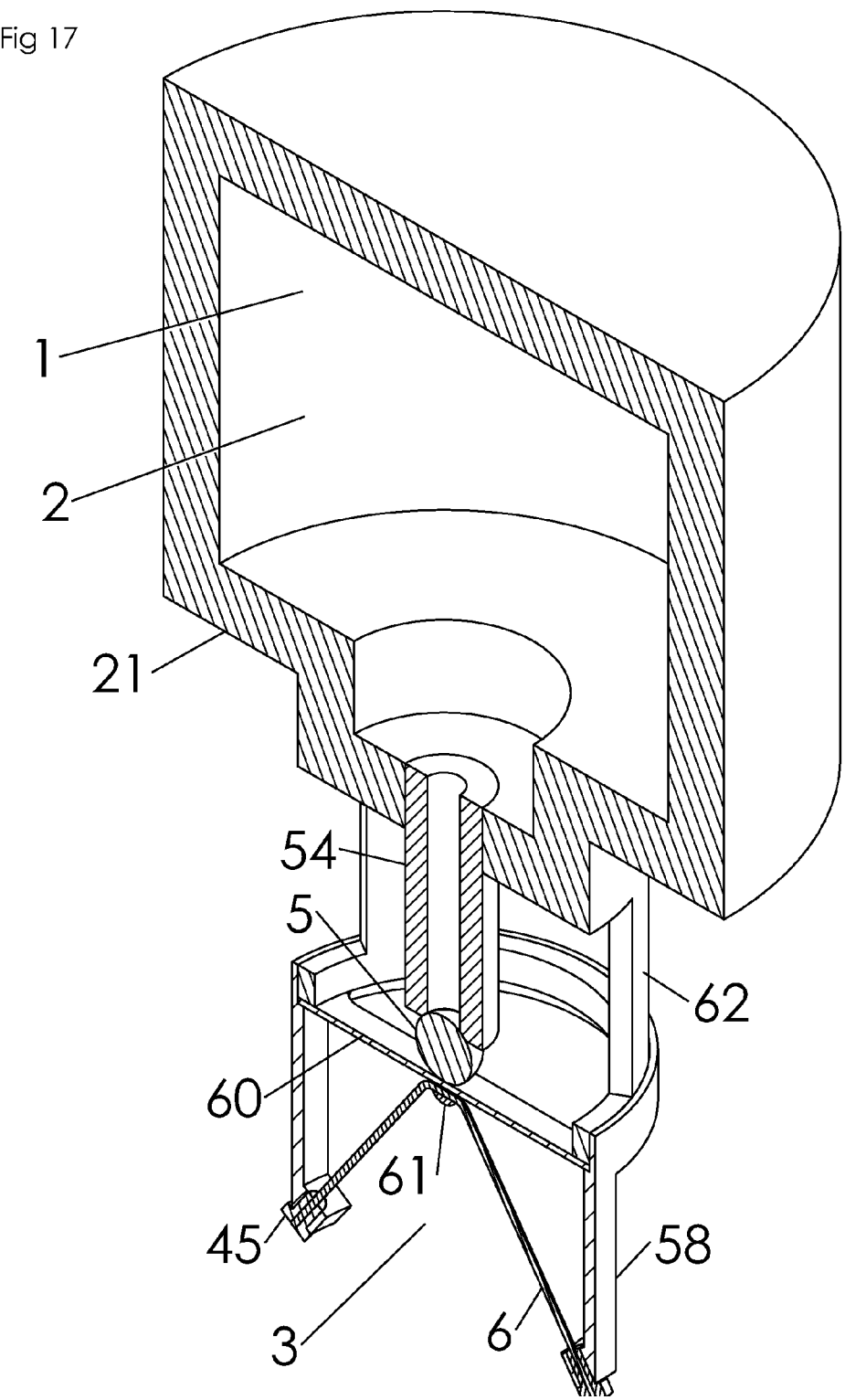

ELECTRONICALLY-CONTROLLED, HIGH PRESSURE FLOW CONTROL VALVE AND METHOD OF USE

RELATED APPLICATIONS

The present application claims priority under 35 U.S.C. §119 of U.S. Application Ser. No. 61/151,393 filed Feb. 10, 2009.

STATEMENT REGARDING FEDERALLY SPONSORED RESEARCH AND DEVELOPMENT

The present invention was partially made with Government support under grant R44HL066830 awarded by the US National Heart Lung and Blood Institute and R44CA096409 awarded by the US National Cancer Institute, National Institutes of Health. The Government has certain rights in the invention.

FIELD OF THE INVENTION

The present invention relates to methods and apparatus for high pressure fluid flow control. In more specific embodiments, the present invention relates to an improved, propellant-driven medical inhaler device for producing respirable aerosols of biologically-active substances, and to methods of using such devices. In further embodiments, the invention relates to electronically-controlled high pressure fluid flow valves and to devices and methods employing such valves, for example, to improve the performance of aerosol devices for aerosolized drug inhalation.

BACKGROUND OF THE INVENTION

Control of low flow rates of high pressure fluids is important in many fields including, but not limited to, supercritical fluid extraction, supercritical fluid chromatography, critical point drying, high pressure small parts cleaning, petrochemical processing, and biofuels production. Accordingly, the device in the present invention can be used advantageously in these fields to improve flow control of the high pressure fluids involved.

A very common method of administering biologically-active substances, such as asthma drugs, to the lungs involves the generation of respirable aerosols from pressurized metered dose inhalers (pMDIs). The typical pMDI comprises a small canister containing a suspension of drug particles or solution of dissolved drug in a compressed liquid propellant such as, formerly, CFC-11 and/or CFC-12, or, currently, HFA-134a. A mechanical means is used to fill a metering chamber with the pressurized suspension, and the chamber is allowed to decompress and spray out into an inhalation zone, flash evaporating the propellant and releasing airborne drug particles. Aerosols are generated by both the gas expansion energy and solvent evaporation.

Hand-held pressurized metered-dose inhalers (pMDIs) are commonly used to deliver bronchodilators and anti-inflammatory drugs to the lungs to treat asthma and chronic obstructive pulmonary diseases. Effective and safe aerosol delivery of pharmaceuticals to the lungs is limited by the solvents and propellants that can be used in inhalers. Until recently chlorofluorocarbon (CFC) propellants 11 (trichlorofluoromethane) and 12 (dichlorodifluoromethane) were the most commonly used propellant gases, but their use has been largely phased out in accordance with the Montreal Protocol due to the ozone-depleting properties of CFC propellants. Alternative propellants for pMDIs have become a necessary pursuit of the pharmaceutical industry. The Montreal Protocol is an international treaty that was drafted in 1987 to phase out the commercial production of all ozone-depleting CFCs. The US FDA, EPA, and DOE each have programs to eliminate production and use of all CFCs. The US FDA will not accept new drug applications for any MDI formulations that use CFCs as propellants. The EPA is expecting the pharmaceutical industry to comply with the Montreal Protocol as soon as proven alternative aerosol delivery techniques are developed for most pharmaceuticals.

Valves used to control high pressure fluid flow at low flow rates are problematic. U.S. Pat. No. 6,032,836 teaches that a metering chamber system can be used to deliver aliquots of high pressure fluid propellants such as liquid carbon dioxide to a low pressure inhalation zone, using a chamfered chamber region with a typical volume of 50 µL around a push pin mounted transversely to a high pressure inlet and low pressure outlet, for manual movement of the chamber from filling to discharging positions. Notably, the dose metering is based on the common approach of physically moving a metering chamber from a filling to discharging position, so it shares the drawbacks of this approach with standard, lower-pressure pMDIs charged with CFC or HFA propellants.

Unfortunately, pMDIs based on prior art have several problems and drawbacks. Notably, metered dose inhalers dispense aliquots of drug-containing propellant suspensions by capturing a small, fixed volume in a movable chamber under pressure and then opening this fixed volume chamber to room atmosphere so that the propellant can expand and drive the drug particles to become airborne. Such an approach has the problem that the movable chamber used to capture the aliquot is of fixed volume, so that the delivered drug amount is subject to change as the density of the propellant changes due to temperature changes, number of doses already administered from the canister, or other means. Plus, even under ideal temperature storage conditions, the dose size is fixed, and cannot be adjusted.

SUMMARY OF THE INVENTION

The present invention is provided to overcome one or more disadvantages of the prior art.

In one embodiment, the invention is directed to a fluid flow control valve which comprises (a) a high pressure region adapted to contain a fluid at its supercritical or nearcritical temperature and pressure conditions and connected via an orifice to a low pressure region, (b) a seat adjacent the orifice, (c) a sealing element positionable against the seat to form a seal between the high pressure region and the low pressure region, and (d) an electrically and/or electronically controlled actuator operable to move the sealing element against and/or away from the seat to allow control of fluid flow from the high pressure region to the low pressure region. In a specific embodiment, the high pressure region contains a fluid at its supercritical or nearcritical temperature and pressure conditions and the fluid comprises carbon dioxide, nitrogen, ethanol, difluoromethane, 1,1,1,2-tetrafluoroethane, or 1,1,1,2,3,3-heptafluoropropane, or a mixture of two or more thereof. The valve may be used, for example, to provide very low flow rates, for example, for supercritical fluid chromatography, supercritical fluid extraction, critical point drying, supercritical fluid cleaning, and supercritical fluid separation methods. In another embodiment, the valve is suitable for use in methods of delivering a biologically active substance to a patient in need thereof.

In another embodiment, the invention is directed to fluid flow control valve for aerosol delivery of biologically active materials for inhalation administration. The valve comprises (a) a high pressure region containing a pressurizable fluid and connected via an orifice to a low pressure region from which inhalation is conducted, (b) one or more biologically active substances dissolved and/or suspended in the pressurizable fluid, (c) a seat adjacent the orifice, (d) a sealing element positionable against the seat to form a seal between the high pressure region and the low pressure region, (e) an electrically and/or electronically controlled actuator operable to move the sealing element against and/or away from the seat to allow control of fluid flow from the high pressure region to the low pressure region, and (f) one or more electronic components operable to perform one or more functions of metered dose inhalation.

Additional features and embodiments of the invention will be apparent form the following detailed description.

BRIEF DESCRIPTION OF THE DRAWINGS

Specific embodiments and features of the invention are depicted in the figures, using reference numerals as indicated, and these embodiments and features are illustrative and non-limiting of the invention described herein, wherein:

FIG. 16 is a schematic diagram depicting the valve of the invention in another embodiment.

FIG. 17 is a schematic diagram depicting the valve of the invention in another embodiment.

Figure 1:
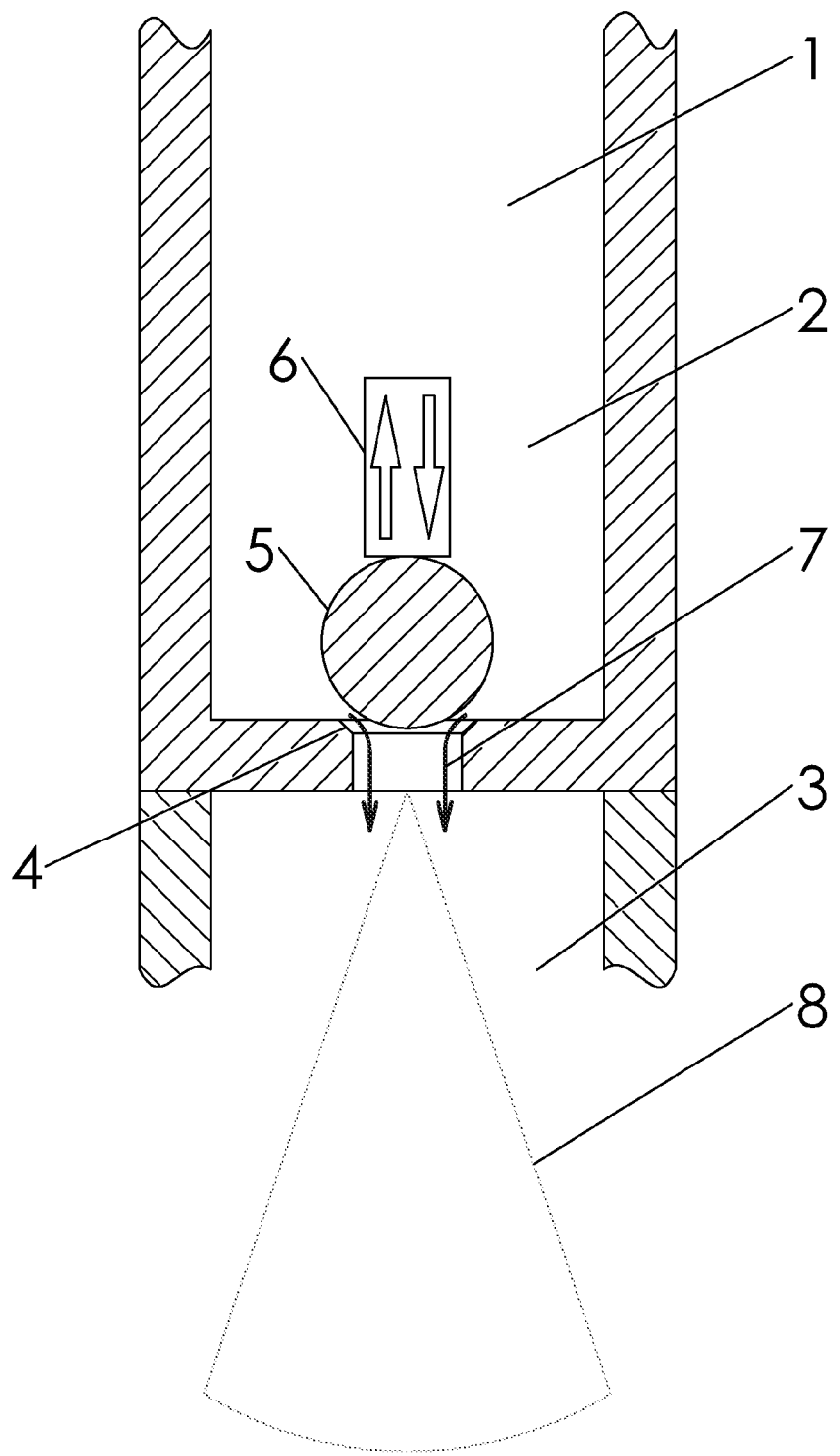
FIG. 1 is a schematic diagram depicting a cross section of the valve assembly (the valve) of the invention in a first embodiment.

The drawings will be more fully understood in view of the detailed description.

DETAILED DESCRIPTION

The invention provides various advantages in certain embodiments. For example, it is an advantage in certain embodiments of the invention to provide an electronically-controlled valve, which allows for improved control and easy record-keeping functions compared to mechanical valves currently used in high pressure fluid flow control valves in general and pressurized metered dose inhalers in particular.

It is a further advantage in certain embodiments of the invention that said electronically-controlled high pressure fluid control valve overcomes the problems of low flow rate control commonly associated with other valves currently used to control the flow of high pressure fluids, allowing precise metering of the flow of high pressure fluids instead of simply being in a discrete on or off state. This advantage can be realized in the present invention by variable valve opening, by controlled duration of valve opening, by controlled duration and frequency of rapid valve open/close cycling, or by a combination of such mechanisms.

It is a further advantage in certain embodiments of the invention that said electronically-controlled valve can be designed, tuned, and/or programmed to improve dose reproducibility relative to mechanically-controlled valves by compensating for temperature, doses already delivered, amount of propellant remaining in the canister, storage conditions between discharges, and other variables.

It is a further advantage in certain embodiments of the invention that said electronically-controlled valve can be programmed to allow adjustment of the delivered dose size based on the needs of the individual patient using it.

It is a further advantage in certain embodiments of the invention that said electronically-controlled valve can be programmed to prevent medication misuse and/or overdose by limiting the number of doses, controlling the minimum time between doses, requiring patient identification prior to dose delivery, counting doses delivered and/or remaining, and other relevant parameters.

It is a further advantage in certain embodiments of the invention that said electronically-controlled valve utilizes an electronic control system which facilitates control of oscillation frequency, pulse width modulation, vibration timing and amplitude, and other means to control the timing and repetition of valve opening and closure.

It is a further advantage in certain embodiments of the invention to provide a valve system which overcomes the problems of solids formation at the low pressure side of valves used to control flow of high pressure carbon dioxide solutions.

From the detailed description and diagrams herein, a number of additional advantages in certain embodiments of the present invention are evident: 1. The electronic control system can include an LCD counter display which can provide a 3 digit resolution counter for showing doses taken and doses remaining in the device. The electronic control system may work easier for dose counting than mechanical or other valve systems. 2. The electronically-controlled inhaler can notify audibly and/or visually when it is close to or at the last dose.

3. Electronic temperature compensation allows the electronically-controlled pMDI to be used at high and low temperatures, allowing its use in a broader temperature range than mechanical or other uncompensated pMDI systems. 4. Electronic counter can also be used for the electronically-controlled pMDI to self-compensate for pressure drop when the device is gradually emptied. 5. The electronically-controlled valve may not require a wasted priming puff.

Embodiments of the invention are depicted in FIGS. 1-17. To facilitate clarity in the description of crucial aspects of the invention, well-known components, well-known electrical circuits, well-known fittings, and well-known procedures are not described in detail. The invention can, of course, take the form of additional embodiments, so the embodiments that are described are intended to describe and teach the invention without limiting the specific details of the invention.

The following reference numerals are used to designate the respective elements:

DRAWINGS

REFERENCE NUMERALS

Figure 2:
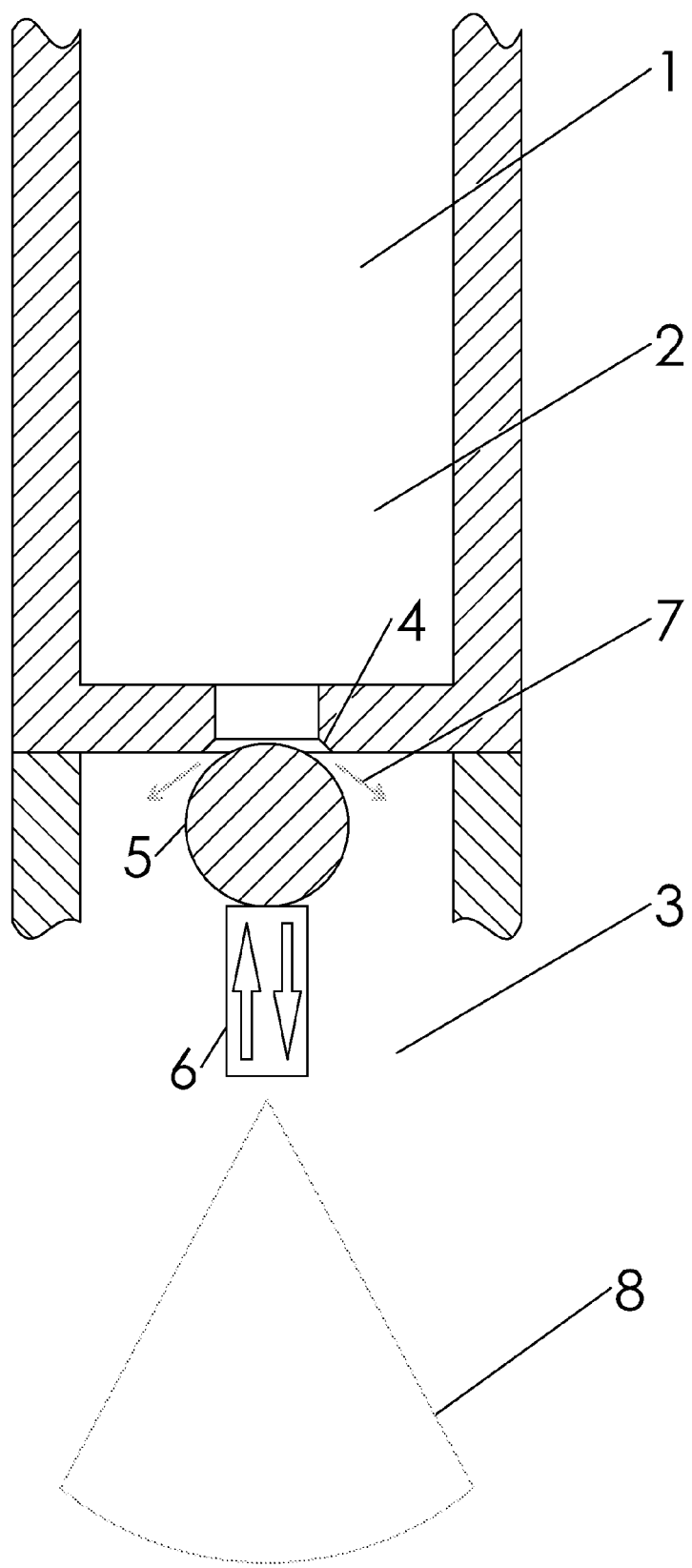
FIG. 2 is a schematic diagram depicting a cross section of the valve of the invention in another embodiment.
Figure 3:
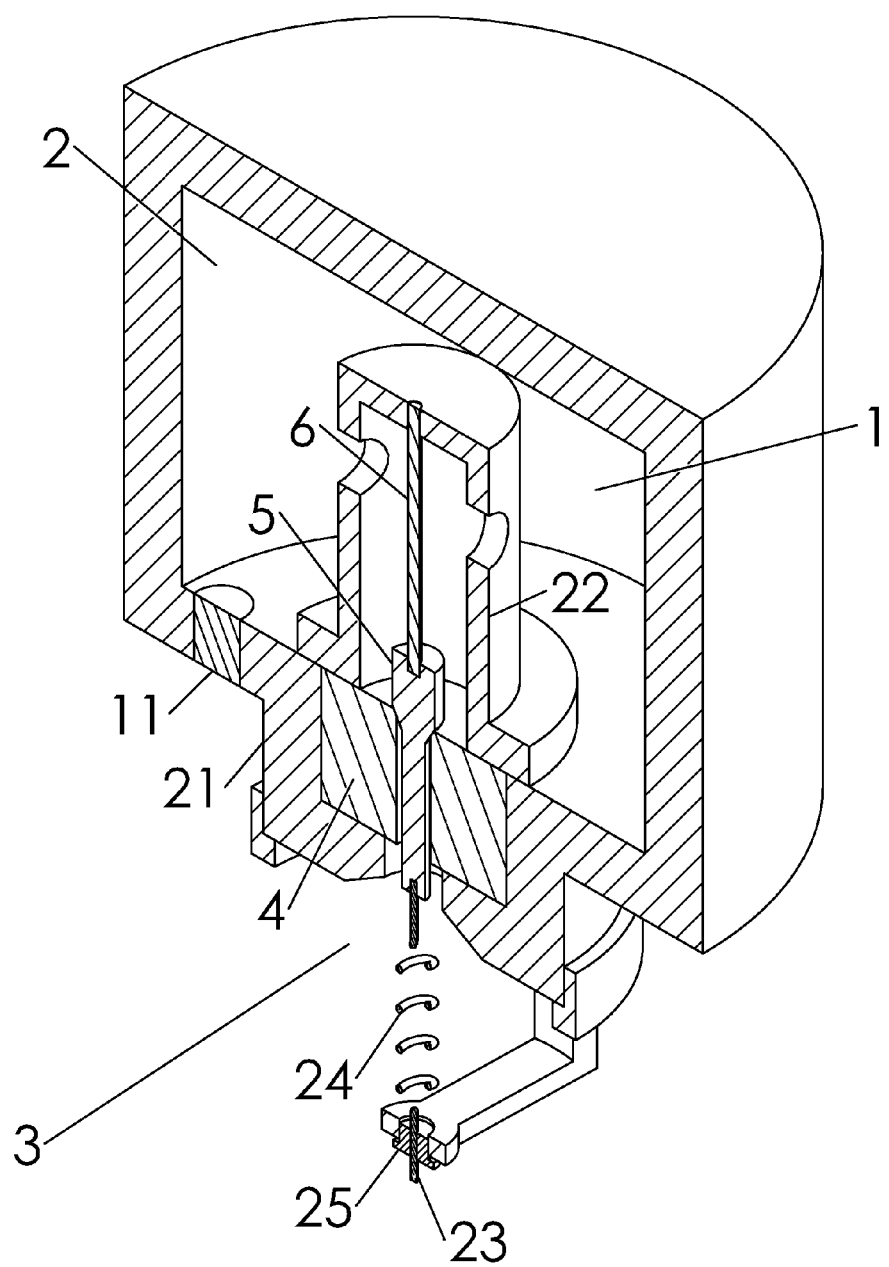
FIG. 3 is a schematic diagram depicting a cross section of the valve of the invention in another embodiment.
Figure 4:
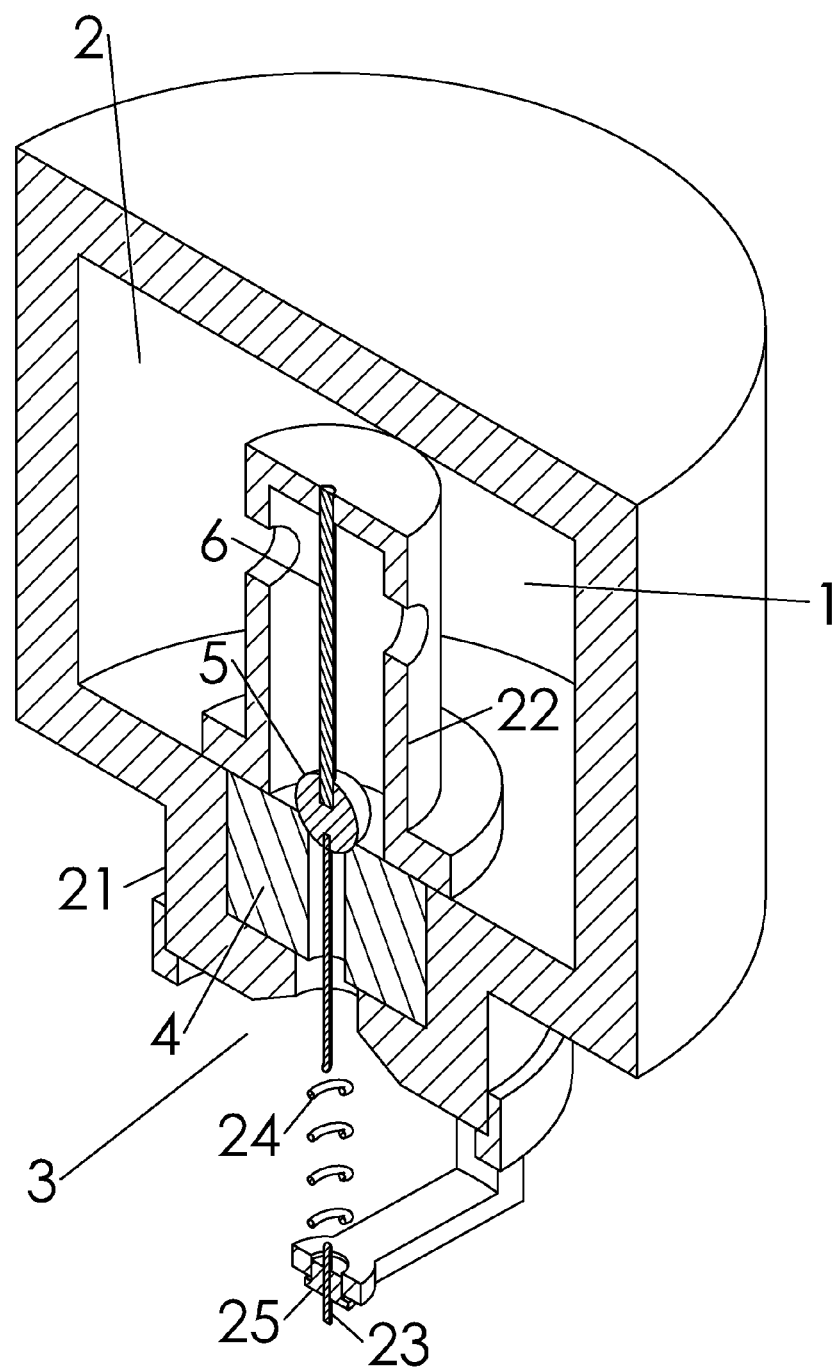
FIG. 4 is a schematic diagram depicting a cross section of the valve of the invention in another embodiment.

1 high pressure region
2 pressurized fluid solution and/or suspension
3 low pressure region
4 seat
5 valve body
6 actuator
7 movement of fluid
8 plume of expanded fluid and aerosol particles
11 valve for pressure relief or filling or both
12 electrical connector
20 piezoelectric actuator
21 high pressure vessel
22 electrically-conductive standoff
23 electrically-conductive tether
24 electrically-conductive spring
25 electrically-insulating fastener
26 rigid beam
27 adjustable pushing pin
28 lever arm
29 Fulcrum
30 pushing means
31 Insulator
32 mounting arms
33 pushing pin
34 support pin
35 rigid mounting arm
36 pushing means
37 Post
38 support for electromagnetic windings
39 permanent ring magnet
40 permeable flux ring
41 permeable back material
42 nonconductive standoff
43 Fastener
44 U-shaped bimetal strip
45 insulating fastener
46 Wire
47 pressure seal insulator
50 piezoelectric disk
51 metal disk
52 adjustable mounting stud
53 mounting nut
54 exit tube
55 sealing film
56 threaded hole
57 leaf spring
58 rigid mounting arm
60 elastic beam
61 attachment point
62 mounting cylinder
63 electromagnetic wire windings
64 pushing means
65 magnetically permeable movable member
66 magnetically permeable housing
67 pushing means
68 bimetal strip
70 electric wire
71 Insulator
72 electric wire In its simplest form, as depicted in FIG. 1 and FIG. 2, the invented valve assembly comprises a high pressure region 1 containing a pressurized fluid solution and/or suspension 2, a low pressure region 3, a seat 4, a valve body 5 which, when in the closed position, creates a seal between the high and low pressure regions, and an actuator 6 which, when engaged to open the valve, displaces the valve body and allows the movement 7 of said fluid from the high pressure region to the low pressure region, creating a plume of expanded fluid and aerosol particles 8. The seat and valve body can be positioned within the low pressure region (FIG. 1) or, alternatively, within the high pressure region (FIG. 2). The actuator is preferably an electronically-controlled means to push or pull the valve body to displace it from the seat. Within the present description, electronically controlled is defined to mean that passing electric current through a component of the actuator causes the actuator to move and overcome a bias to push or pull the seal from the seat. Discontinuing the flow of current through the actuator component discontinues the force causing movement and the bias returns the seal to the seat. One of ordinary skill in the art will appreciate that the flow of current may be controlled in various respects, including rate and duration, to selectively dispense aerosol particles. In specific embodiments as discussed in detail below, the movement of the actuator can be achieved through contraction or expansion of a component or by generation of an electromagnetic force. Other embodiments resulting in movement of the actuator within the scope of the present invention will be apparent to one of ordinary skill in the art in view of the present disclosure.

FIG. 1 is a diagram depicting the valve assembly (valve) of the invention in a first embodiment. A high pressure region 1 containing a high pressure fluid and dissolved or suspended drug substance 2, and a low pressure region 3 are separated by a valve body 5 positioned inside the high pressure region such that when the valve body is in the closed position it creates a seal against a seat 4 between the high and low pressure regions, and which can be opened by an electronically-driven actuator 6 and allow release at 7 of fluid and drug from the high pressure region to the low pressure region, and expansion of the fluid which forms an aerosol plume 8. Notably, other pressurized fluids can be utilized instead of carbon dioxide in this invention, with those skilled in the art recognizing that the supercritical fluid solvent can be selected from a list of pressurized solvents including, but not limited to, carbon dioxide, HFC-134a (1,1,1,2-tetrafluoroethane), and HFC-227 (1,1,1,2,3,3,3-heptafluoropropane, aka HFC-227ea). Advantages to the general form of this embodiment with the valve body 5 in the high pressure region 1 include the use of such design as a fill valve to force high pressure fluids into the high pressure region.

FIG. 2 is a diagram depicting another embodiment of the valve assembly of the invention. A high pressure region 1 containing a high pressure fluid and dissolved or suspended drug substance 2, and a low pressure region 3 are separated by a valve body 5 positioned in the low pressure region such that when the valve body is in the closed position it creates a seal against a seat 4 between the high and low pressure regions, and which can be opened by an electronically-driven actuator 6 and allow release at 7 of fluid and drug from the high pressure region to the low pressure region, and expansion of the fluid which forms an aerosol plume 8. Notably, other pressurized fluids can be utilized instead of carbon dioxide in this invention, with those skilled in the art recognizing that the supercritical fluid solvent can be selected from a list of pressurized solvents including, but not limited to, carbon dioxide, HFC-134a (1,1,1,2-tetrafluoroethane), and HFC-227 (1,1,1,2,3,3,3-heptafluoropropane, aka HFC-227ea). Notably, this arrangement with the valve body 5 positioned in the low pressure region allows it to act as a pressure relief valve in case the pressure in the high pressure region 1 gets too high, because the actuator 6 can be adjusted so that it presses the valve body 5 against the set 4 with a low enough force that overpressure in the high pressure region 1 can force it open, making it the primary pathway for relief of pressure from the high pressure region 1. Advantages to the general form of this embodiment with the valve body 5 in the low pressure region 1 include the aforementioned pressure relief valve usage and simplified electrical connectivity to valve components.

Hand held inhaler devices incorporating the present invention were built and tested for aerosol size distribution using pharmaceuticals that are commonly used for asthma treatment. In specific embodiments, pressurized carbon dioxide ($CO_2$) was employed, and several advantages to the use of pressurized $CO_2$ were established:

1. $CO_2$ is a suitable MDI propellant replacement because it has zero ozone depletion potential and a global warming potential less than 0.1% of the new HFA propellants
2. $CO_2$ MDI propellant generates aerosols in a narrow size range that are most likely to reach the lungs.
3. $CO_2$ is the only propellant that can stimulate deep breathing and increase the deposition of aerosols in the lungs for more efficient delivery of pharmaceuticals.
4. Many of the surfactants and solvent modifiers approved for inhaler formulations are very soluble in carbon dioxide.
5. Many of the pharmaceuticals that are currently used to treat asthma are soluble in carbon dioxide.
6. The toxicology of carbon dioxide is well understood because it has been in our lungs throughout human existence and has been used extensively in anesthesiology (especially Europe)
7. The low reactivity of carbon dioxide is well known because it has been extensively studied for pharmaceutical extraction and processing.
8. The high energy expansion of carbon dioxide can generate respirable aerosols of viscous liquids and sticky solids that cannot be collected for dry powder inhalers.
9. Carbon dioxide has been used to generate pharmaceutical aerosols that have not been generated by any other method.
10. Carbon dioxide MDIs can be used for both local lung therapy and systemic drug delivery.

FIGS. 3-17 disclose additional embodiments of the invention.

In another embodiment, depicted in FIG. 3, the actuator 6 comprises a shape memory alloy (SMA) wire 6 mounted within the high pressure region 1 by attachment to an electrically-conductive standoff 22 and connected to an electrically-conductive valve body 5 which in this embodiment is pin-shaped and seated against an electrically-insulating seat 4 and pulled down into sealing position in the low pressure region 3 by an electrically-conductive tether 23 which is partially coiled into a spring form 24, electrically-isolated at the low pressure end by insulator 25, so that when electrical current is passed through the shape memory alloy (SMA) wire actuator 6, it contracts and breaks the seal between the valve body 5 in the form of a pin and the seat 4 so that the high pressure fluid 2 contained within the vessel 21 is allowed to be released into the low pressure region 3. The SMA wire material can include, but is not limited to, a nickel titanium alloy known as Nitinol in which heat treatment while under stress to stretch the material results in an elongated shape which attempts to revert back to its original shape when heated to a temperature above its transformation temperature, as accomplished by resistive heating in the present example. Also depicted in this embodiment is a valve 11 for filling, pressure relief, or both, adding advantages of convenient filling and pressurization and enhanced safety.

In another embodiment, depicted in FIG. 4, the actuator 6 comprises a shape memory alloy (SMA) wire 6 mounted within the high pressure region 1 by attachment to an electrically-conductive standoff 22 and connected to an electrically-conductive valve body 5 which in this embodiment is ball-shaped and seated against an electrically-insulating seat 4 and pulled down into sealing position in the low pressure region 3 by an electrically-conductive tether 23 which is partially coiled into a spring form 24, electrically-isolated at the low pressure end by insulator 25, so that when electrical current is passed through the SMA wire actuator 6, it contracts and breaks the seal between the valve body 5 in the form of a ball and the seat 4 so that the high pressure fluid 2 contained within the vessel 21 is allowed to be released into the low pressure region 3.

In another embodiment, depicted in FIG. 5, the actuator 6 comprises a shape memory alloy (SMA) wire 6 mounted within the high pressure region 1 by attachment to an electrically-conductive standoff 22 and connected to an electrically-conductive valve body 5 which, in this embodiment, is pin-shaped and seated against an electrically-insulating seat 4, so that when electrical current is passed through the electrical connector 12, the pin 5, the SMA wire actuator 6, the electrically conductive standoff 22, and the electrically conductive pressure vessel body 21, the SMA wire contracts and breaks the seal between the valve body 5 and the seat 4 so that the high pressure fluid 2 contained within the vessel 21 is allowed to be released into the low pressure region 3. The internal pressure in the high pressure region 1 holds the pin in a position which facilitates sealing and resealing after opening.

In another embodiment, depicted in FIG. 6, the actuator comprises a pushing means such as a piezoelectric actuator 20 pushing across an intervening insulator 71 to a lever arm 28 mounted to a fulcrum 29. The lever arm includes at the opposite end an adjustable push pin 27 pressing on a sealing element 5, which in this example is ball-shaped, to seat it against the sealing seat 4 when in the closed position and thereby contain the fluid and dissolved or suspended drug 2 in the high pressure region 1 contained within a high pressure vessel 21. In this embodiment, when the piezoelectric actuator 20 is induced to contract by passing electric current through it via electric wire 70 and either through a second electric wire at its other end where it contacts the pressure vessel 21 or through electrical contact of the piezoelectric actuator 20 to the pressure vessel 21 and grounding of said vessel at another location, said contraction allows the sealing element 5 to unseat from the sealing seat 4, allowing high pressure fluid and dissolved or suspended drug 2 to be released from the high pressure vessel 21 into the low pressure region 3.

Figure 7:
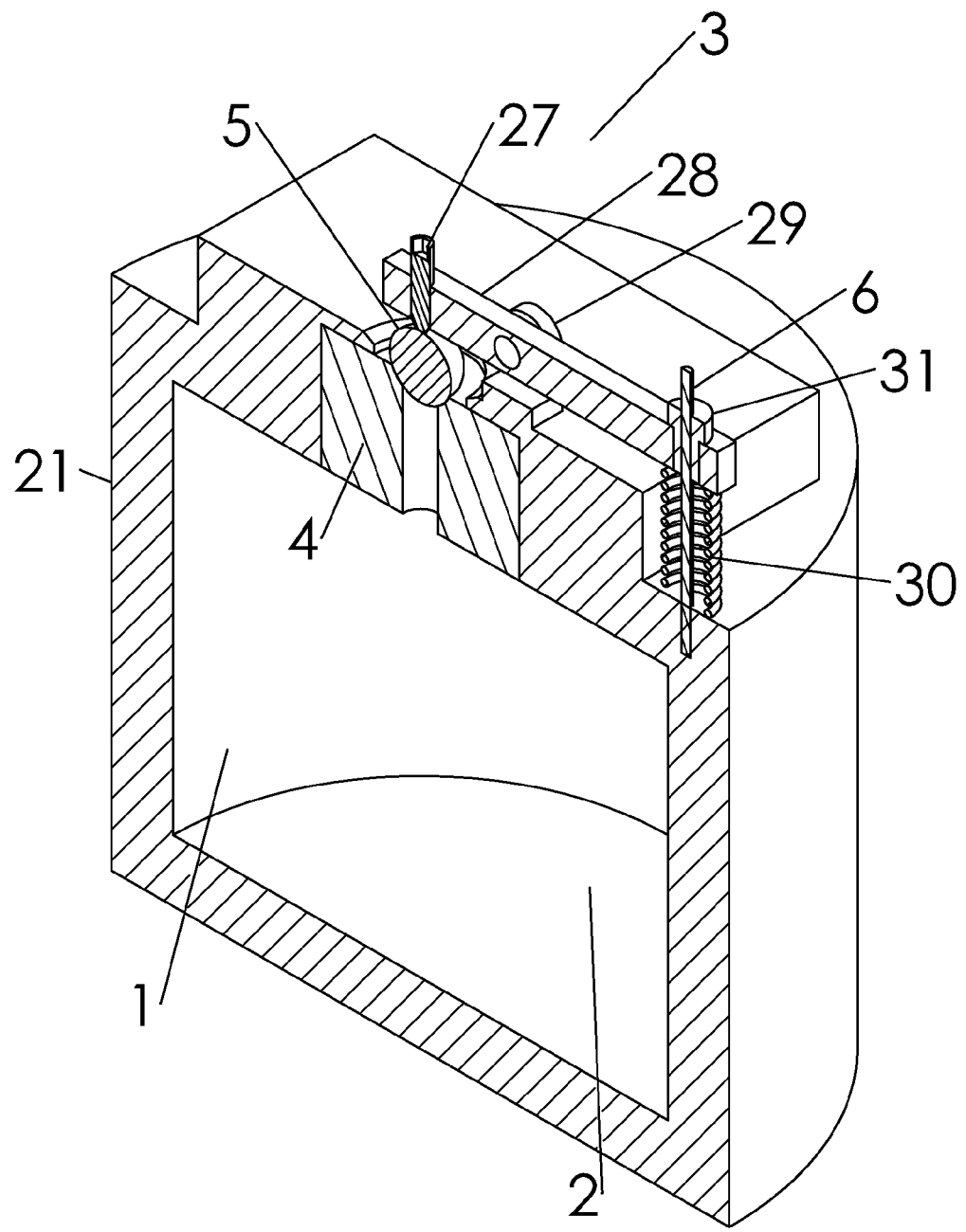
FIG. 7 is a schematic diagram depicting a cross section of the valve of the invention in another embodiment.

In another embodiment, depicted in FIG. 7, the actuator 6 comprises a shape memory alloy (SMA) wire 6 mounted in the low pressure region 3 by attachment with an intervening insulator 31 to a lever arm 28 pivoting on a fulcrum 29 with the opposite end pressed with a spring or other pushing means 30 so that the adjustable pin 27 in said lever arm presses a sealing means 5, which in this embodiment is ball-shaped, to seat it against the sealing seat 4 when in the closed position and thereby contain the fluid and dissolved or suspended drug 2 in the high pressure region 1 contained within a high pressure vessel 21. The arm 28 can be made thin enough to apply spring force itself to the pin 27 and sealing means 5. In this embodiment, when electrical current is passed through the SMA wire actuator 6, it contracts and pulls the lever arm 28 hard enough to overcome the pushing means 30, such as a spring, and unseat the sealing means 5 from the sealing seat 4, allowing high pressure fluid and dissolved or suspended drug 2 to be released from the high pressure vessel 21 into the low pressure region 3.

Figure 8:
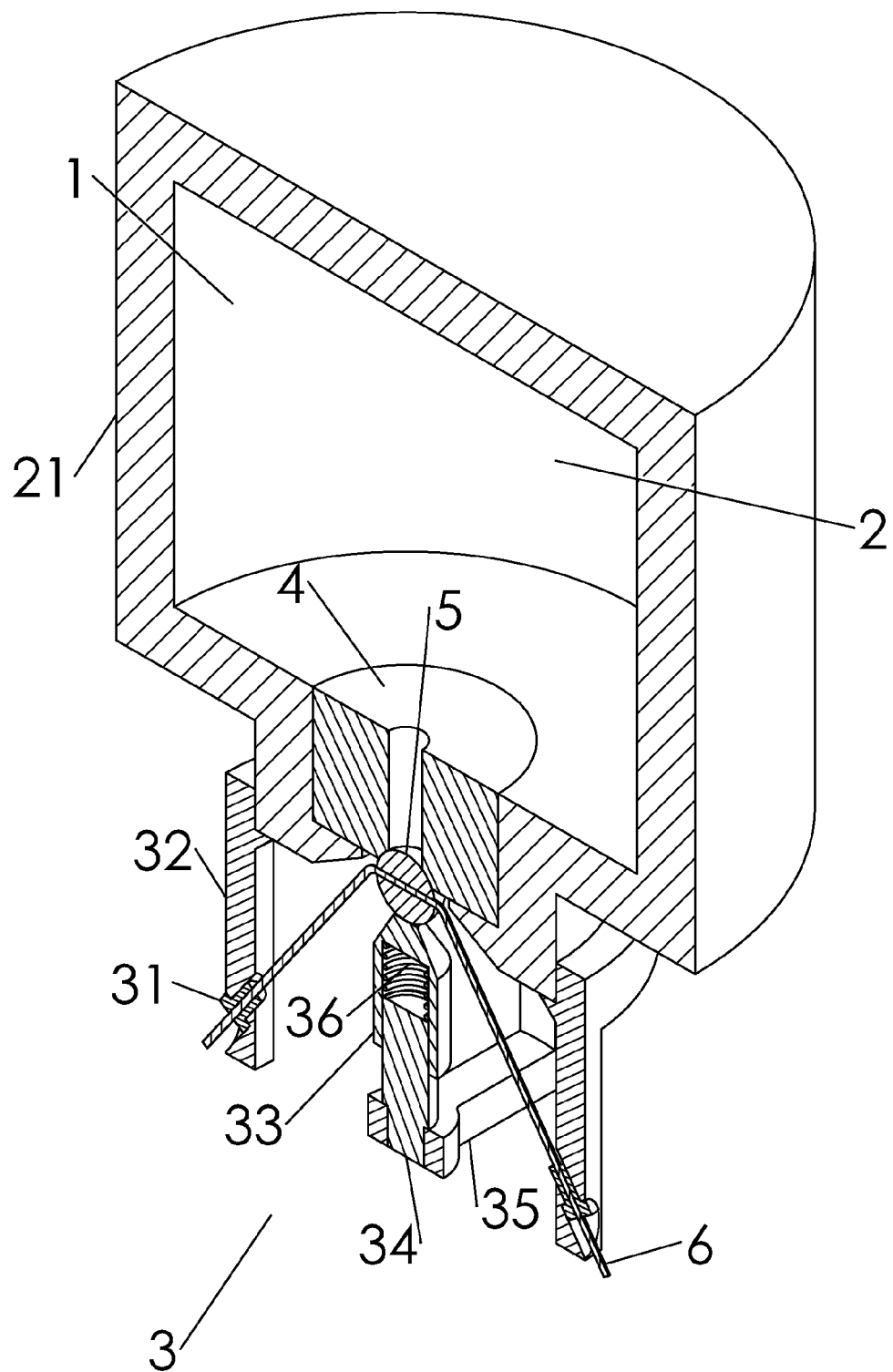
FIG. 8 is a schematic diagram a cross section of depicting the valve of the invention in another embodiment.

In another embodiment, depicted in FIG. 8, the actuator 6 comprises a shape memory alloy (SMA) wire 6 mounted in the low pressure region 3 by attachment of each end of 6 using insulators 31 to mounting arms 32 out from the sealing seat 4 and with said SMA wire 6 connected to the sealing means 5 which in this embodiment is ball-shaped and seated against a seat 4 when in the closed position. Said sealing means 5 is pressed against said seat 4 by a pushing pin 33 that has adjustable position by its connection to a support pin 34 mounted to a rigid mounting arm 35 and including a pushing means 36, such as a spring, so that when electrical current is passed through the SMA actuator 6, it pulls the sealing means 5 away from the sealing seat to break the seal between the sealing means ball 5 and the seat 4 so that the high pressure fluid and dissolved or suspended drug 2 contained within the vessel 21 is allowed to be released into the low pressure region 3. This embodiment has the advantage that the cooling effect of the fluid expansion from the high pressure region 1 to the low pressure region 3 cools the SMA wire actuator 6, reducing the response time and improving control.

Figure 9:
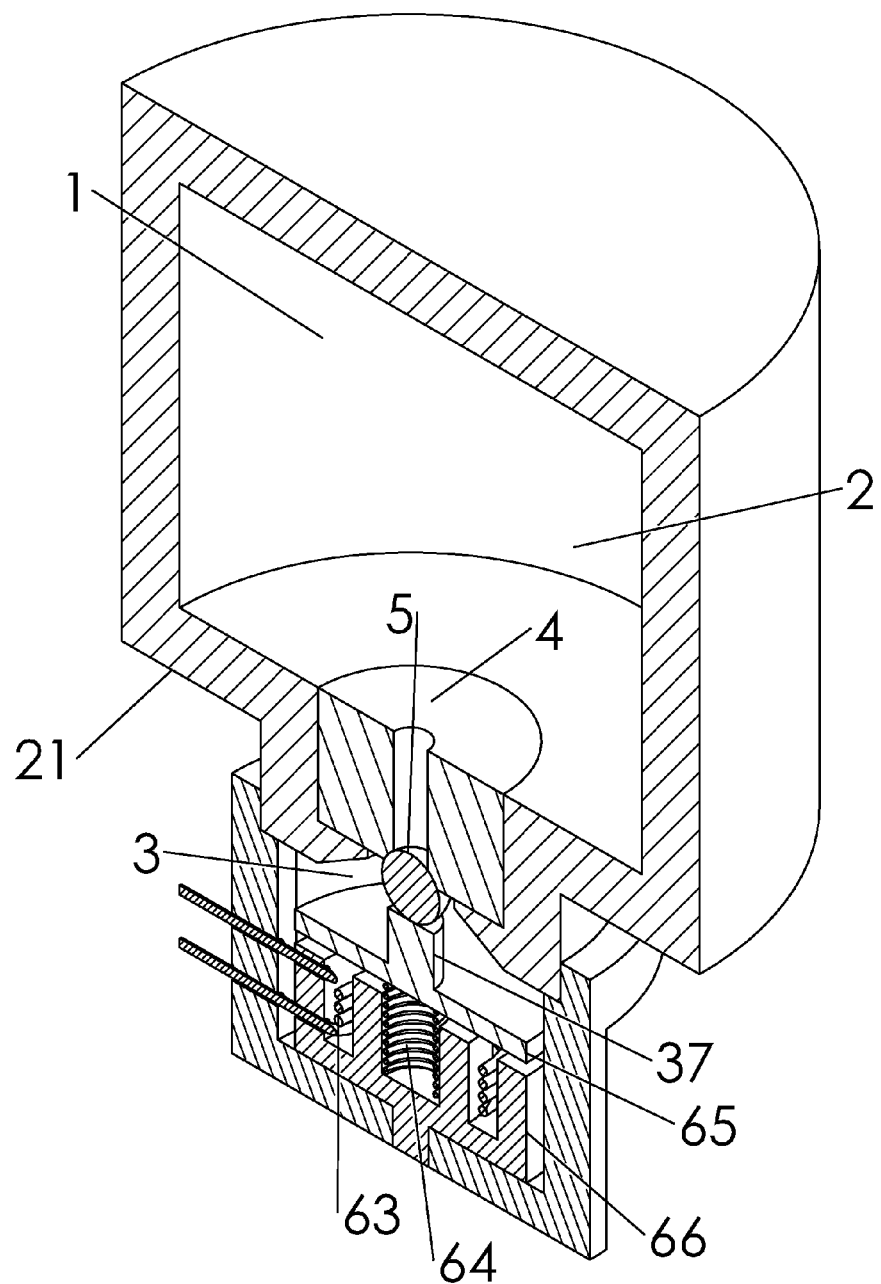
FIG. 9 is a schematic diagram depicting a cross section of the valve of the invention in another embodiment.

In another embodiment, depicted in FIG. 9, the actuator comprises a magnetically permeable movable member 65 with a push post 37 exerting force against a valve body 5, which is ball-shaped in this embodiment, to press it against a seat 4 when in the closed position to create a seal and capture the high pressure fluid and dissolved or suspended drug 2 within the high pressure region 1 contained within the pressure vessel 21. The moveable member 65 and post 37 are pressed into position by a pushing means 64, such as a spring, with enough force to seat the valve body 5 against the seat 4, and when electrical current is directed through the electromagnetic wire windings 63 wound around a magnetically permeable housing 66 a magnetic field is generated which attracts the moveable member 65 towards the pushing means 64 with enough force and/or momentum to open the seal between the valve body ball 5 and the seat 4 so that the high pressure fluid and dissolved or suspended drug 2 contained within the vessel 21 is allowed to be released into the low pressure region 3.

Figure 10:
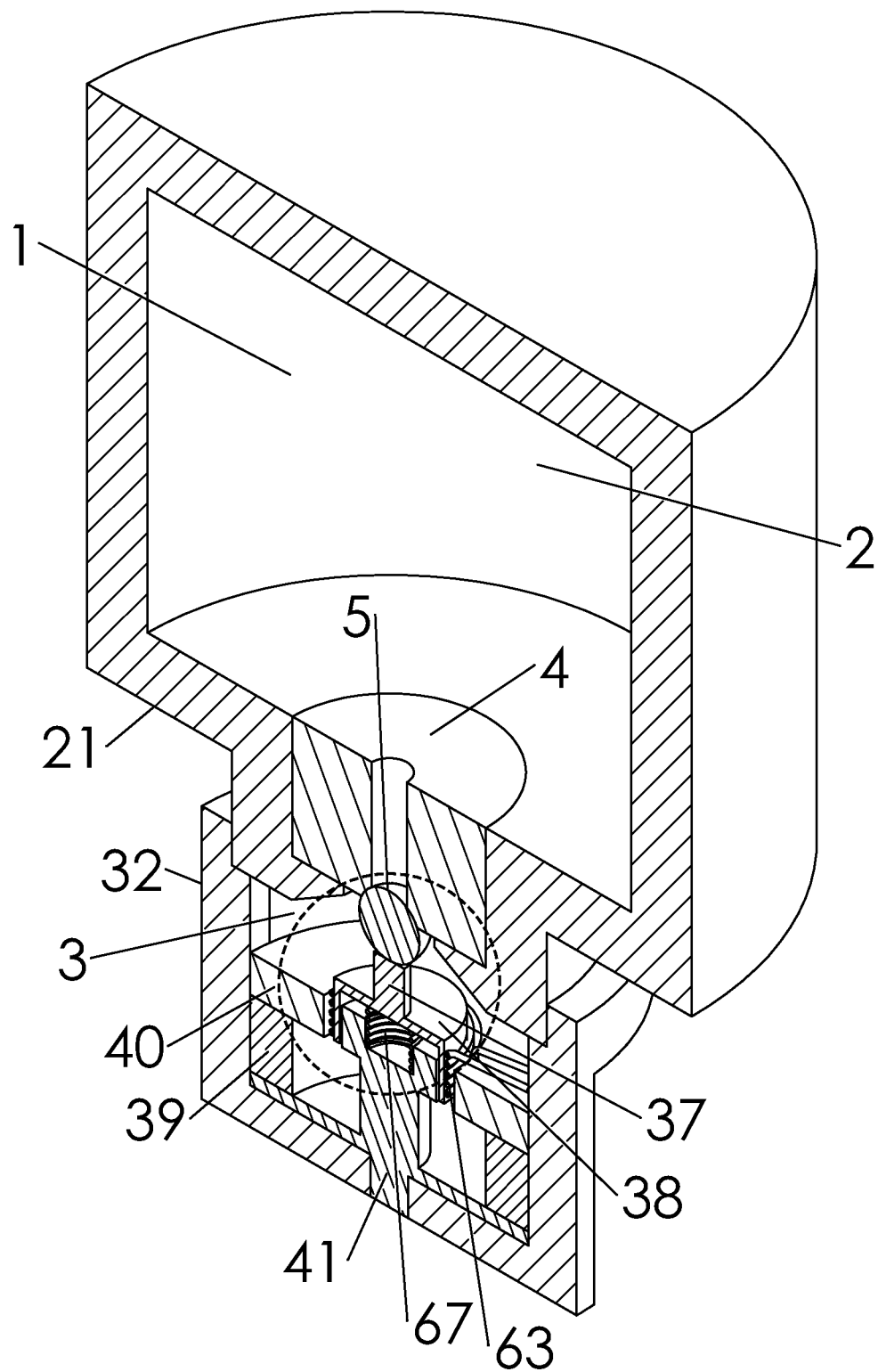
FIG. 10A is a schematic diagram depicting a cross section of the valve of the invention in another embodiment.
FIG. 10B shows an enlarged view of the indicated portion of FIG. 10A.
Figure 10:
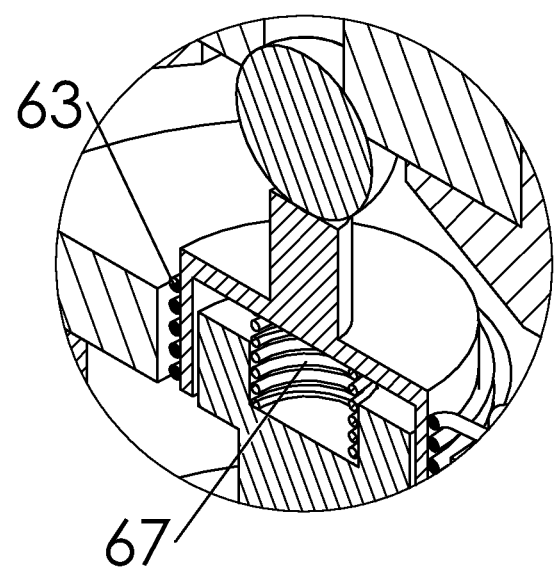

In another embodiment, depicted in FIG. 10, the actuator comprises a support for electromagnetic windings 38, such as in a voice coil, integrally bonded to electromagnetic wire windings 63 and with a push post 37 exerting force against a valve body 5, which is ball-shaped in this embodiment, to press it against a seat 4 when in the closed position to create a seal and capture the high pressure fluid and dissolved or suspended drug 2 within the high pressure region 1 contained within the pressure vessel 21. The support for electromagnetic windings 38 and post 37 are pressed into position by a pushing means 67, such as a spring, with enough force and/or momentum to seat the valve body 5 against the seat 4, and when electrical current is directed through the electromagnetic wire windings 63 bound to the voice coil housing, a magnetic field is generated which attracts the support for electromagnetic windings 38 towards the permanent ring magnet 39 using magnetic flux traveling through a permeable flux ring 40 and permeable back material 41, so that the support for electromagnetic windings 38 and post 37 are pulled towards the pushing means 67 with enough force and/ or momentum to open the seal between the valve body 5 and the seat 4 so that the high pressure fluid and dissolved or suspended drug 2 contained within the vessel 21 is allowed to be released into the low pressure region 3.

Figure 11:
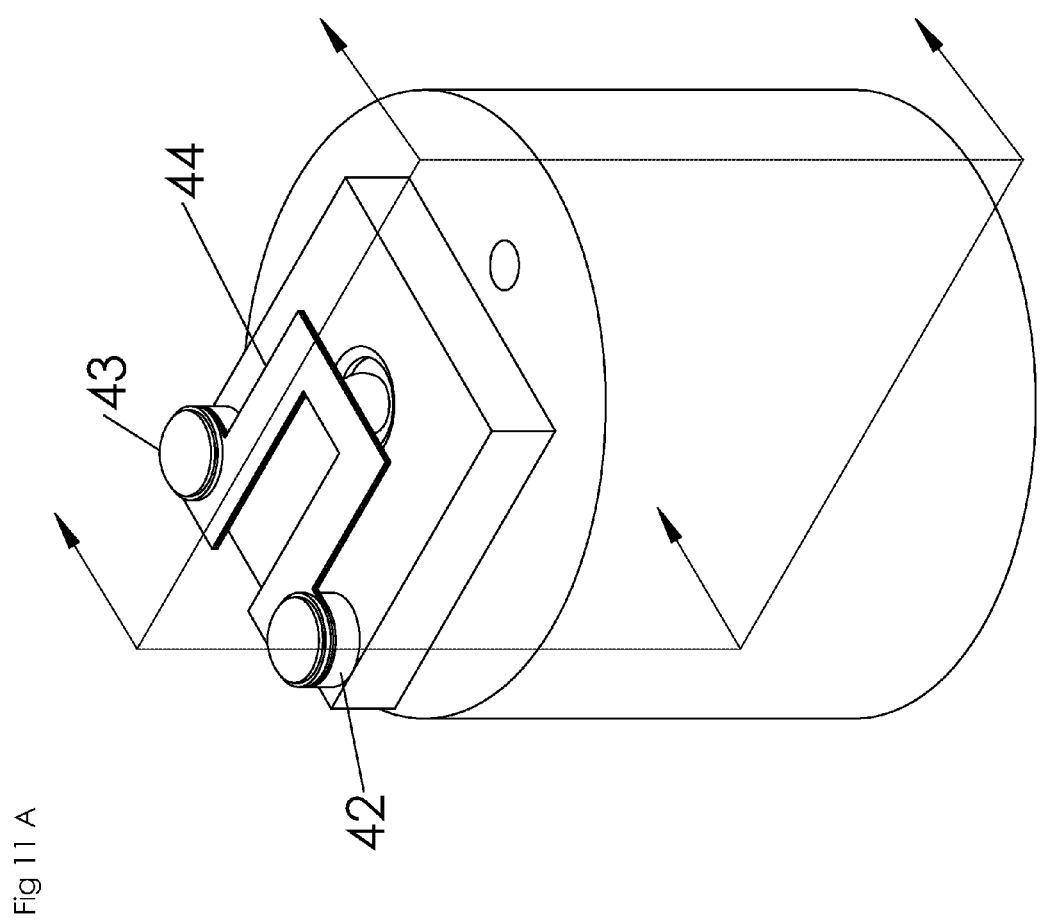
FIG. 11A shows a perspective view depicting the valve of the invention in another embodiment.
FIG. 11B is a schematic diagram depicting a cross section of the valve of FIG. 11A, taken along the plane shown in FIG. 11A.
Figure 11:
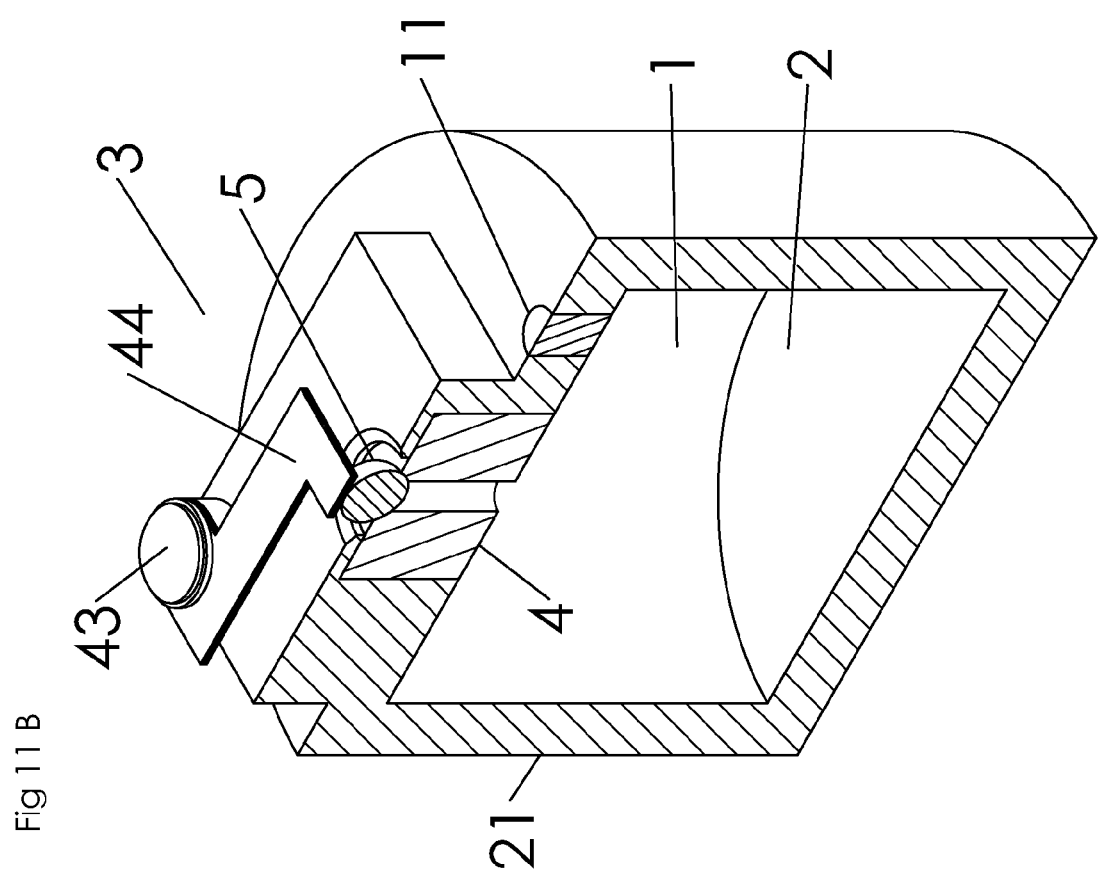

In another embodiment, depicted in FIG. 11, the actuator comprises a U-shaped bimetal strip 44 mounted in the low pressure region 3 by attachment of each end of 44 using nonconductive standoffs 42 and fasteners 43 so that the middle of the U-shape of the bimetal strip presses against a sealing means 5 which in this embodiment is ball-shaped and seats it against a seat 4 when in the closed position. Said U-shaped bimetal strip 44 is preloaded to force the sealing means 5 against the seat 4, and when electrical current is passed through the U-shaped bimetal strip 44, it bends away from the sealing means 5 and the sealing seat 4, breaking the seal between the sealing means 5 and the seat 4 so that the high pressure fluid and dissolved or suspended drug 2 contained in the high pressure region 1 within the vessel 21 is allowed to be released into the low pressure region 3. The amount of flow allow to be released from the high pressure region 1 is controlled by the intensity and duration of the electrical pulse applied through the bimetal strip. This embodiment has the advantage that the cooling effect of the fluid expansion from the high pressure region 1 to the low pressure region 3 cools the bimetal strip 44, reducing the response time and improving control. In this embodiment is also depicted a fill or pressure relief valve 11.

Figure 12:
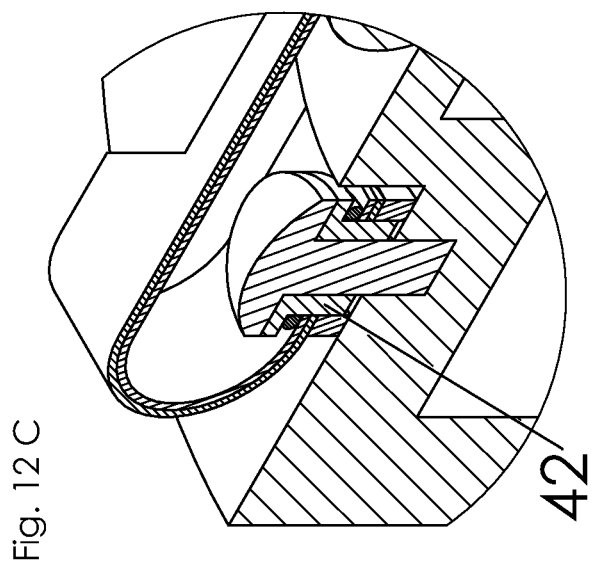
FIG. 12A shows a perspective view depicting the valve of the invention in another embodiment.
FIG. 12B is a schematic diagram depicting a cross section of the valve of FIG. 12A, taken along the plane shown in FIG. 12A.
FIG. 12C shows an enlarged view of the indicated portion of FIG. 12B.

In another embodiment, depicted in FIG. 12, the actuator comprises a bimetal strip 68 mounted in the low pressure region 3 in a spring-like fashion by rolling over each end of 68 and attaching each end of 68 using nonconductive standoffs 42 and fasteners 43 so that the middle of said bimetal strip presses against a sealing means 5 which in this embodiment is ball-shaped and seats said sealing means 5 against a sealing seat 4 when in the closed position. Said bimetal strip 68 is preloaded to force the sealing means 5 against the seat 4, and when electrical current is passed through the bimetal strip 68, it bends away from the sealing means 5 and the sealing seat 4, breaking the seal between the sealing means 5 and the seat 4 so that the high pressure fluid and dissolved or suspended drug 2 contained in the high pressure region 1 within the vessel 21 is allowed to be released into the low pressure region 3. In typical use, the center of the bimetal strip 68 would be narrower than the ends so that the voltage drop is higher at the site of contact with the sealing means 5. In this way, when current is passed through the bimetal strip 68, using for example electric wire 72 to connect to each end of said bimetal strip, most of the heating and deflection occurs in the narrow region of the bimetal strip 68, and cooling of the bimetal strip 68 occurs due to the expanding fluid flow, which serves to improve valve control. In this embodiment is also depicted a valve 11 used for filling and/or pressure relief purposes.

Figure 13:
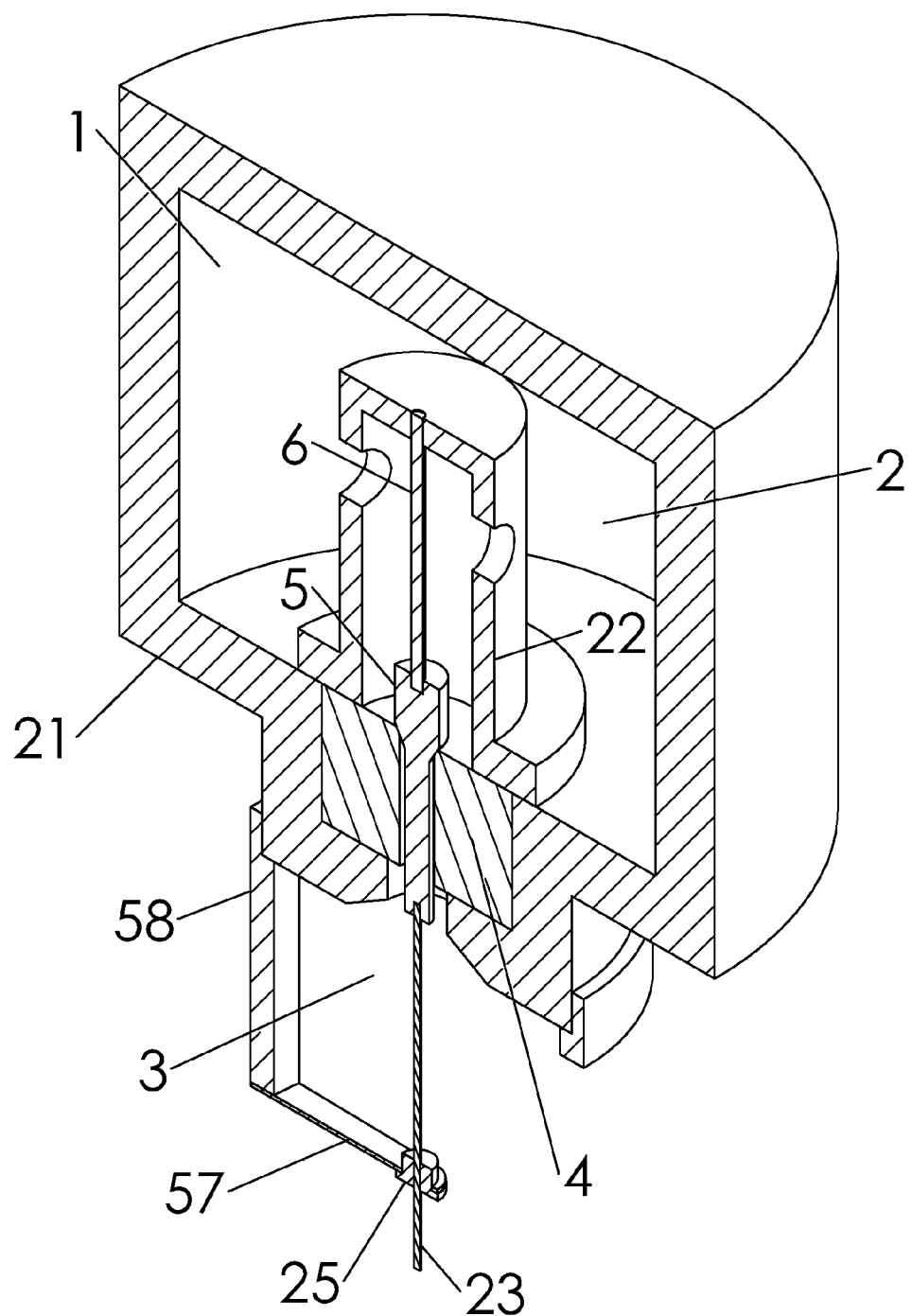
FIG. 13 is a schematic diagram depicting the valve of the invention in another embodiment.

In another embodiment, depicted in FIG. 13, the actuator 6 comprises a shape memory alloy (SMA) wire 6 mounted within the high pressure region 1 by attachment to an electrically-conductive standoff 22, in this example a rigid metal tubular structure, and connected to an electrically-conductive valve body 5, which in this embodiment is pin-shaped and seated against an electrically-insulating seat 4, and pushed down into sealing position by pressure in the high pressure region 1 and pulled down into sealing position by an electrically-conductive tether 23 in the low pressure region 3 such that said tether 23 is attached using an electrically insulating fastener 25 to a leaf spring 57 attached to the pressure vessel 21 by means of a rigid mounting arm 58, so that the valve body 5 is pulled into a sealing position by the leaf spring 57 when in the closed position but when electrical current is passed through the SMA wire actuator 6, it contracts and breaks the seal between the valve body 5 and the seat 4 so that the high pressure fluid 2 contained within the vessel 21 is allowed to be released into the low pressure region 3. Further, when no current is passed through the SMA wire 6, the leaf spring 57 and the internal pressure in the high pressure region 1 within the pressure vessel 21 both facilitate reseating of the valve body 5 against the seat 4, stopping the release of high pressure fluid and drug 2 from the pressure vessel 21 into the low pressure region 3. This embodiment has the advantage that the heated SMA wire actuator 6 in the high pressure region 1 allows preheating of the high pressure fluid during actuation of the valve.

Figure 14:
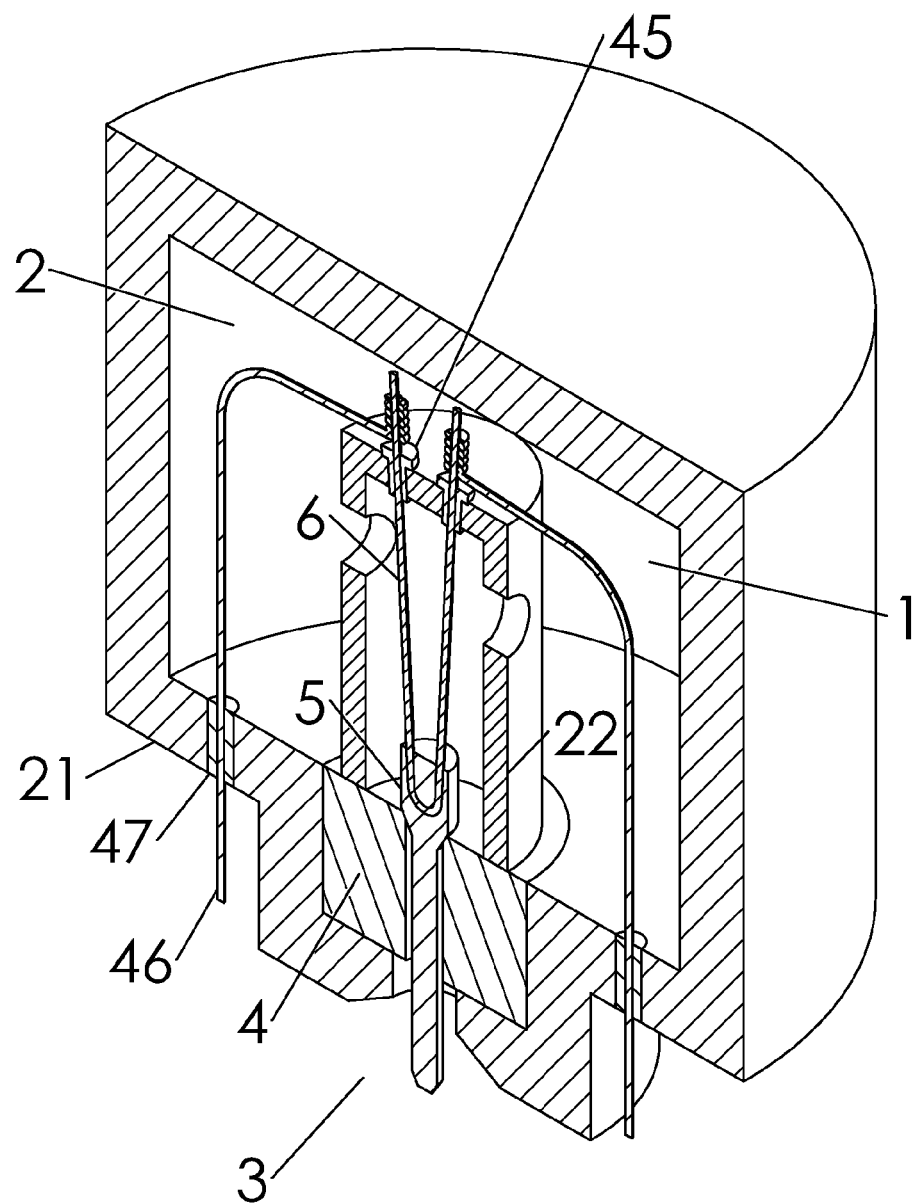
FIG. 14 is a schematic diagram depicting the valve of the invention in another embodiment.

In another embodiment, depicted in FIG. 14, the actuator 6 comprises a shape memory alloy (SMA) wire 6 with a bend in the middle mounted within the high pressure region 1 by passing each end of the SMA wire 6 through insulating fasteners 45 and attachment of fastener 45 to a standoff 22 and fastening of each end of the SMA wire 6 to the standoff by means of the insulating fasteners 45. Said SMA wire 6 is connected at said bend in middle to a valve body 5, which in this embodiment is pin-shaped and seated against a seat 4 and pushed down into sealing position by pressure in the high pressure region 1 when in the closed position. Each end of the SMA wire 6 is further connected to conductive wires 46 which pass through pressure seal insulators 47 facilitating the passage of electrical current from access to the wires 46 in the low pressure region 3 to actuate the SMA wire 6 so that it contracts and pulls the valve body 5 away from the seat 4 so that the seal is broken and the high pressure fluid and drug 2 contained in the high pressure region 1 within the vessel 21 is allowed to be released into the low pressure region 3.

Figure 15:
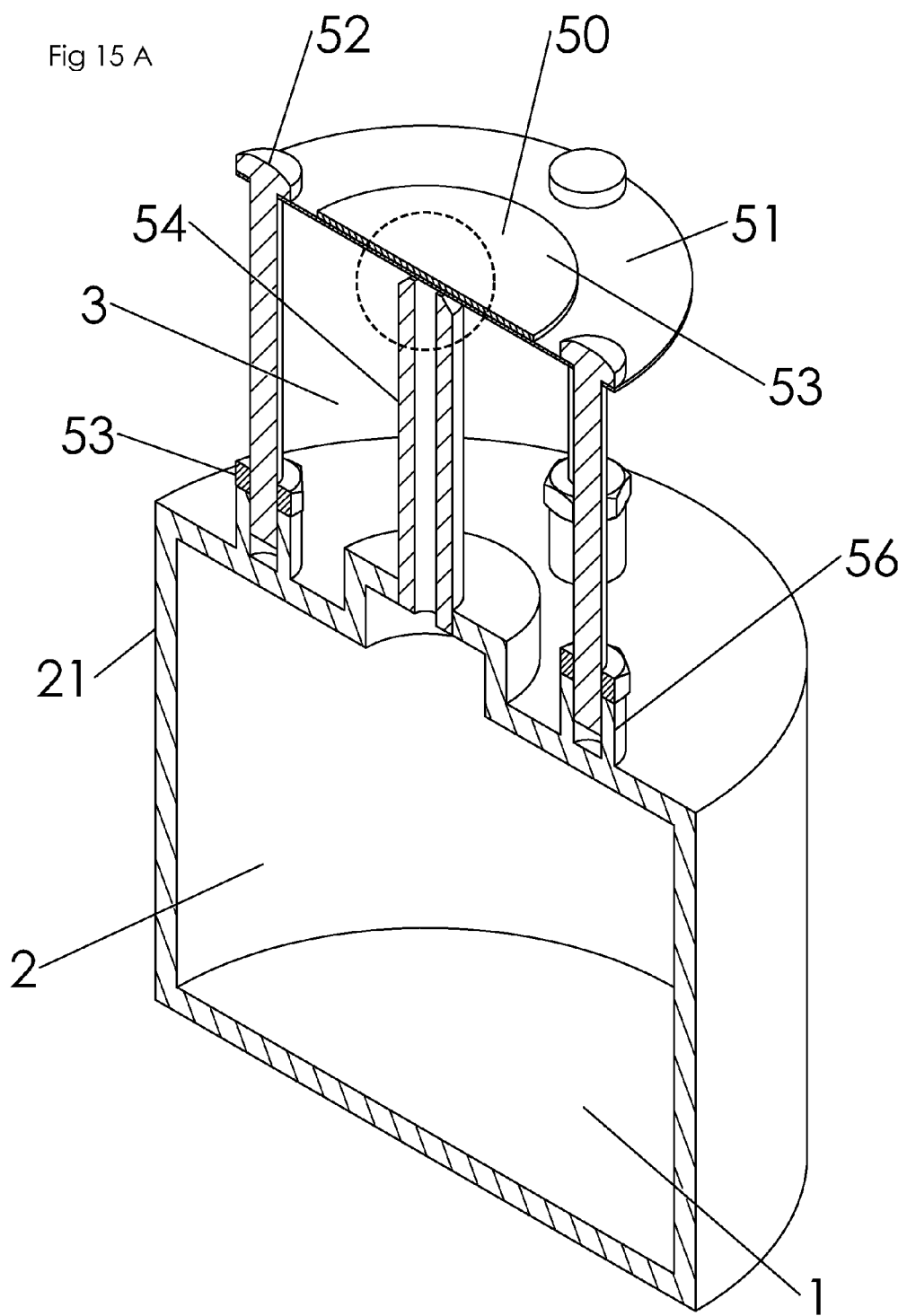
FIG. 15A is a schematic diagram depicting a cross section of the valve of the invention in another embodiment.
FIG. 15B shows an enlarged view of the indicated portion of FIG. 15A.
Figure 15:
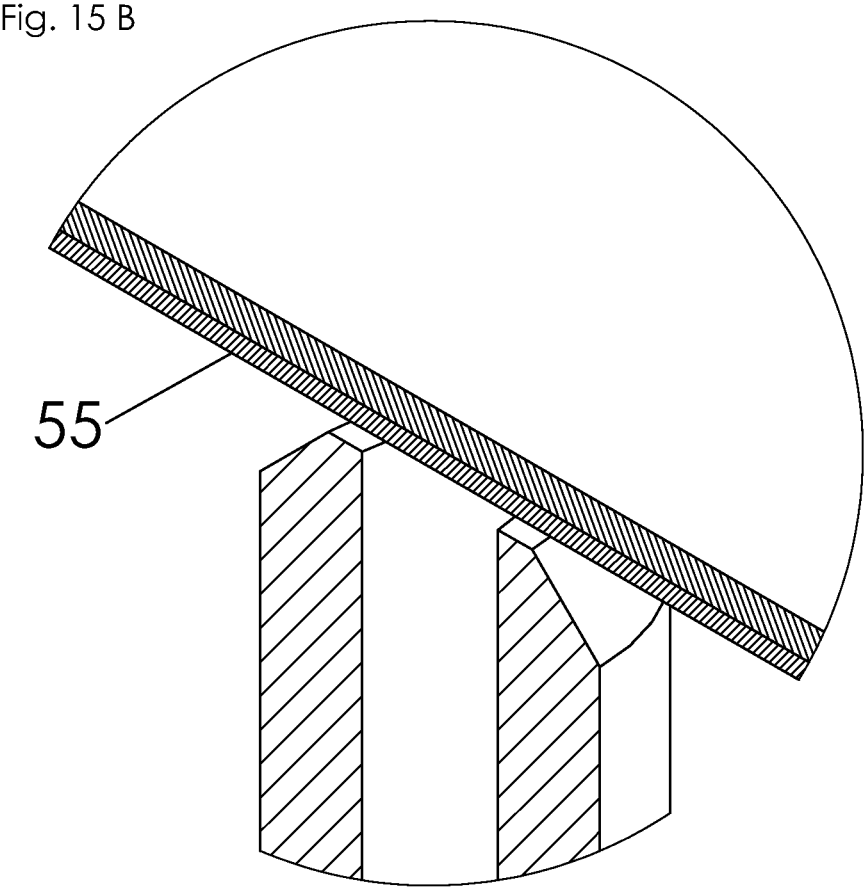

In another embodiment, depicted in FIG. 15, the actuator comprises a piezoelectric disk 50 conductively and mechanically bonded to a metal disk 51 mounted to the pressure vessel 21 by means of a multiplicity of adjustable mounting studs 52 threaded into mounting nuts 53 and threaded holes 56 attached to the pressure vessel 21. Location of said bonded piezoelectric disk 50 and metal disk 51 are adjusted so that a sealing film 55 bonded to the disk 51 surface opposite the piezoelectric disk 50 presses against an exit tube 54 attached to the pressure vessel 21 so that the inside of the tube 54 is contiguous with the high pressure region 1 containing the pressurized fluid and drug 2 and so that the contact between the sealing film 55 and the exit tube 54 create a seal and prevent the high pressure fluid and drug 2 from release into the low pressure region 3 when in the closed position. Further, application of DC bias voltage and/or oscillating voltage to the piezoelectric disk 50 induces it to move and break the seal between the sealing film 55 and the tube 54 allowing controlled release of high pressure fluid and drug 2 contained in the vessel 21 to pass through the tube 54 and out of the open end of the tube 54 into the low pressure region 3.

In another embodiment, depicted in FIG. 16, the actuator comprises a piezoelectric disk 50 conductively bonded to a metal disk 51 mounted to the pressure vessel 21 by means of a multiplicity of adjustable mounting studs 52 threaded into mounting nuts 53 and threaded holes 56 attached to the pressure vessel 21. Location of said bonded piezoelectric disk 50 and metal disk 51 are adjusted so that the disk 51 surface opposite the piezoelectric disk 50 presses against a sealing means 5, in this embodiment ball-shaped, seated at the end of an exit tube 54 which is attached to the pressure vessel 21 so that the inside of the tube 54 is contiguous with the high pressure region 1 containing the pressurized fluid and drug 2. Further, said pressing of the sealing means 5 against the end of the exit tube 54 creates a seal and prevents the high pressure fluid and drug 2 from release into the low pressure region 3 when in the closed position. Further, application of DC bias voltage and/or oscillating voltage to the piezoelectric disk 50 induces it to move and break the seal between the sealing means 5 and the tube 54 allowing controlled release of high pressure fluid and drug 2 contained in the vessel 21 to pass through the tube 54 and out of the open end of the tube 54 into the low pressure region 3.

In another embodiment, depicted in FIG. 17, the actuator 6 comprises a shape memory alloy (SMA) wire 6 mounted in the low pressure region 3 by attachment of each end of 6 using insulating fasteners 45 to rigid mounting arms 58. This embodiment further comprises an exit tube 54 which is attached to the pressure vessel 21 so that the inside of the tube 54 is contiguous with the high pressure region 1 containing the pressurized fluid and drug 2, a mounting cylinder 62 holding a cutaway disk possessing an elastic beam 60 across its center, positioned so that said beam 60 presses against a valve body 5, in this case ball-shaped, seated at the end of said exit tube 54. Further, said pressing of the valve body 5 against the end of the exit tube 54 creates a seal and prevents the high pressure fluid and drug 2 from release into the low pressure region 3 when in the closed position. Further, the SMA wire 6 is attached to the middle of the elastic beam at the middle of the SMA wire 6 by means of an attachment point 61 on the elastic beam such that passage of electrical current through the SMA wire 6 induces it to contract and pull on the elastic beam 60 and break the seal between the valve body 5 and the tube 54 allowing controlled release of high pressure fluid and drug 2 contained in the vessel 21 to pass through the tube 54 and out of the open end of the tube 54 into the low pressure region 3.

Skilled persons will appreciate that the present invention facilitates flow control of high pressure fluids and provides an electronically-controlled valve for use in an electronic metered dose inhaler with many advantages over existing devices.

The following examples illustrate certain embodiments of the invention.

Example 1

Figure 5:
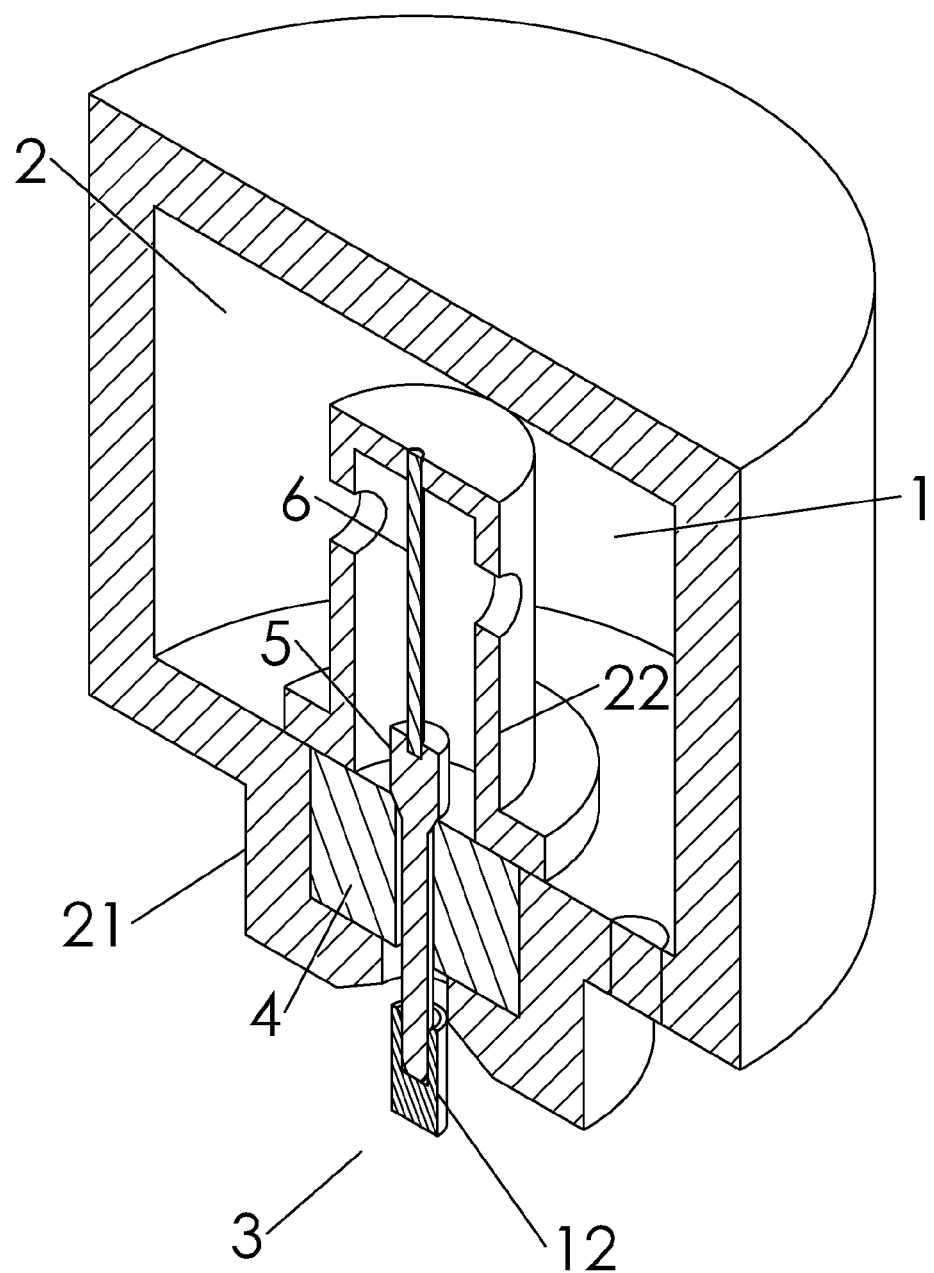
FIG. 5 is a schematic diagram depicting a cross section of the valve of the invention in another embodiment.
Figure 6:
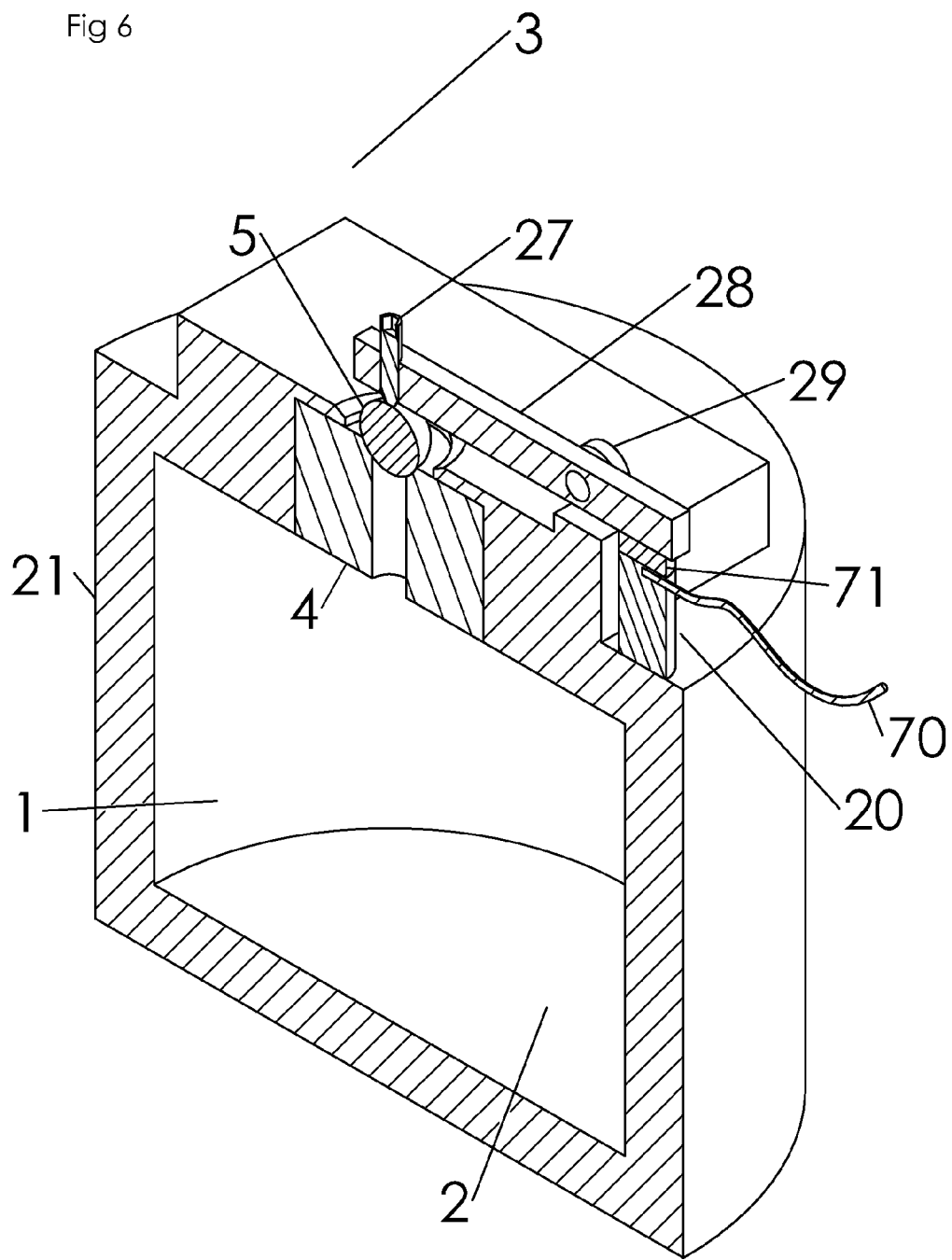
FIG. 6 is a schematic diagram depicting a cross section of the valve of the invention in another embodiment.

A valve according to FIG. 5 is constructed and mounted onto an aluminum canister pressure vessel with an internal volume of 12 mL, incorporating a shape memory alloy actuator wire conductively mounted to an electrically-conductive standoff inside the canister, and a gold-plated metal pin as the sealing element seated against an elastomeric seat. The canister is pressurized to about 900 psi with carbon dioxide, and metered releases of carbon dioxide gas are effected by application of sufficient current to the shape memory alloy wire to cause it to contract and pull the pin away from the seat. After each release of pressurized gas from the canister into room pressure, after stopping the application of DC current to the shape memory alloy wire actuator, the pin returns to the closed position against the seat and the flow stops. The process is repeated several times. Finally, after pressurizing the canister with 2.88 g of carbon dioxide and sealing the canister with the aforementioned gold pin against the elastomeric seat, the leak rate was measured. After 480 days, 97.8% of the originally-loaded carbon dioxide is still contained within the canister, indicating a low leak rate and a good valve seal.

Example 2

A valve according to FIG. 11 is constructed so that the metal ball sealing element, 1 mm diameter, is seated into the end of a 1.6 mm outer diameter stainless steel tube into which an internal beveled edge had been cut to facilitate seating of the ball against the tube. The ball is pressed into place with a U-shaped bimetal strip, preloaded with enough tension to hold the ball sealed against the tube when 2000 psi of pressure is applied inside the tube, and 2000 psi is maintained going into the tube with carbon dioxide. When current is passed through the bimetal strip, it bends away from the tube, sufficiently to allow the ball to move away from the tube and allow carbon dioxide to flow out of the tube into room pressure. It is determined that the flow rate is proportional to the amount of electrical current passed though the bimetal strip, and the valve is demonstrated to open and close through dozens of cycles of applying electrical current.

Example 3

A valve according to FIG. 15 is constructed using a 0.4 mm OD tube through which flow is controlled from a region of 900 psi carbon dioxide to room pressure. A thin layer of polyurethane, approximately 0.2 mm thick, is applied to the surface of a 20 mm diameter brass disk on the opposite side from piezoelectric ceramic material conductively attached to the disk, also known as a piezoelectric bender. The disk is mounted perpendicular to the tube with the urethane coating pressed against the end of the tube with sufficient force to seal the tube against flow of the 900 psi carbon dioxide into the room pressure region. Eighty volts DC are applied to the piezoelectric bender, along with 6 kHz oscillating voltage, which bends the disk away from the tube and allows carbon dioxide flow to exit the tube. This actuation is repeatedly tested for 2500 on/off cycles of 0.8 sec on and about 7 sec off, and the valve is found to repeatedly release metered pulses of carbon dioxide gas and then reseal at the end of the test.

Example 4

A valve according to FIG. 15 is constructed using a 0.4 mm OD tube through which flow is controlled from a region of approximately 80 psi of 1,1,1,2-tetrafluoroethane (HFC-134a) to room pressure. A thin layer of polyurethane, approximately 0.2 mm thick, is applied to the surface of a 20 mm diameter brass disk on the opposite side from piezoelectric ceramic material conductively attached to the disk, also known as a piezoelectric bender. The disk is mounted perpendicular to the tube with the urethane coating pressed against the end of the tube with sufficient force to seal the tube against flow of the 80 psi 1,1,1,2-tetrafluoroethane into the room pressure region. One hundred ten volts DC are applied to the piezoelectric bender, along with oscillating voltage, 8 kHz, 10 volts AC, which bends the disk away from the tube and allows 1,1,1,2-tetrafluoroethane flow to exit the tube. This actuation is repeatedly tested for 1000 on/off cycles of 0.8 sec on and about 7 sec off, and the valve is found to repeatedly release metered pulses of 1,1,1,2-tetrafluoroethane gas and then reseal at the end of the test.

The various examples and embodiments described herein are illustrative in nature only and are non-limiting of the invention defined by the claims.

What is claimed is:

1. An inhaler for aerosol delivery of a biologically active material, comprising:
    a. a high pressure container containing a pressurized fluid and a biologically active material dissolved and/or suspended in the pressurized fluid,
    b. a low pressure region connected via an orifice to the high pressure container, wherein the orifice is configured to deliver the pressurized fluid and biologically active material as an aerosol to the low pressure region and the low pressure region is configured to allow inhalation administration of the aerosol by a user,
    c. a seat adjacent the orifice,
    d. a sealing element positioned against the seat to form a seal between the high pressure container and the low pressure region,
    e. an electrically and/or electronically controlled actuator operable to move the sealing element away from the seat to allow fluid flow from the high pressure container to the low pressure region, and
    f. an electronic component operable to actuate the actuator to meter a dose of the pressurized fluid and biologically active material from the high pressure container through the orifice to the low pressure area where the pressurized fluid and biologically active material are delivered as an aerosol.

2. The inhaler device according to claim 1, wherein the pressurized fluid is at its supercritical or nearcritical temperature and pressure conditions.

3. The inhaler device according to claim 1, wherein the pressurized fluid is at its supercritical or nearcritical temperature and pressure conditions and comprises carbon dioxide, nitrogen, ethanol, difluoromethane, 1,1,1,2-tetrafluoroethane, or 1,1,1,2,3,3,3-heptafluoropropane, or a mixture of two or more thereof.

4. The inhaler device according to claim 3, wherein the actuator is positioned in the low pressure region.

5. The inhaler device according to claim 3, wherein the actuator is positioned in the high pressure container.

6. The inhaler device according to claim 3, wherein the sealing element is a metal pin.

7. The inhaler device according to claim 6, wherein the actuator comprises one or more shape memory alloy wires.

8. The inhaler device according to claim 3, wherein the sealing element is a metal or ceramic ball.

9. The inhaler device according to claim 8, wherein the actuator comprises one or more shape memory alloy wires.

10. The inhaler device according to claim 8, wherein the actuator comprises an electromagnetic coil operable to counteract a spring force holding the sealing element ball against the seat.

11. The inhaler device according to claim 8, wherein the actuator comprises an electromagnetic voice coil assembly.

12. The inhaler device according to claim 8, wherein the actuator comprises a bimetallic strip positioned to press the sealing element ball against the seat and operable to bend away from the seat when current is applied through the actuator.

13. The inhaler device according to claim 3, wherein the sealing element comprises a deformable film on a piezoelectric bender, wherein the piezoelectric bender is positioned to press the film against the seat, and wherein the piezoelectric bender bends away from the orifice when voltage is applied.

14. The inhaler device according to claim 13, wherein the deformable film comprises an elastomeric material.

15. The inhaler device according to claim 14, wherein the elastomeric film comprises polyurethane, fluoropolymer, or polyimide.

16. The inhaler device according to claim 13, wherein the piezoelectric bender is actuated with both a direct current voltage and an alternating current voltage to cause the piezoelectric bender to move away from the orifice and to oscillate away from and towards the orifice.

17. The inhaler device according to claim 3, wherein the actuator comprises a piezoelectric bender.

18. The inhaler device according to claim 17, wherein the piezoelectric bender is actuated with both a direct current voltage and an alternating current voltage to cause the piezoelectric bender to move away from the orifice and to oscillate away from and towards the orifice.

19. The inhaler device according to claim 1, wherein the biologically active substance comprises an agent for treating at least one pulmonary condition.

20. The inhaler device according to claim 19, wherein the pulmonary condition comprises asthma, emphysema, pneumonia, chronic obstructive pulmonary disease, cystic fibrosis, or lung cancer.

21. The inhaler device according to claim 3, further comprising an electronic control operable to trigger, count, record, and/or limit actuations of the valve for metered dose delivery of the biologically active substance to a patient.

22. A method of delivering a biologically active substance to a patient in need thereof, comprising actuating the actuator of the inhaler device of claim 1.

* * * * *